United States Patent
Lin et al.

(10) Patent No.: US 8,785,402 B2
(45) Date of Patent: Jul. 22, 2014

(54) COMPOSITIONS AND ASSAYS FOR TREATMENT AND DIAGNOSIS OF HELICOBACTER PYLORI INFECTION AND CONDITIONS

(75) Inventors: Chun-Hung Lin, Taipei (TW); Ta-Wei Liu, Meinong Township, Kaohsiung County (TW)

(73) Assignee: Academia Sinica, Taipei (TW)

( * ) Notice: Subject to any disclaimer, the term of this patent is extended or adjusted under 35 U.S.C. 154(b) by 492 days.

(21) Appl. No.: 12/806,084

(22) Filed: Aug. 2, 2010

(65) Prior Publication Data
US 2011/0065758 A1 Mar. 17, 2011

Related U.S. Application Data

(60) Provisional application No. 61/230,674, filed on Jul. 31, 2009.

(51) Int. Cl.
| | | |
|---|---|---|
| *A01N 43/04* | (2006.01) | |
| *A61K 31/70* | (2006.01) | |
| *A01N 43/40* | (2006.01) | |
| *A61K 31/445* | (2006.01) | |
| *C07D 211/00* | (2006.01) | |
| *C12N 9/99* | (2006.01) | |

(52) U.S. Cl.
USPC .............. 514/23; 514/315; 435/184; 546/242

(58) Field of Classification Search
CPC . A61K 31/445; C12N 9/00; C12Y 302/01051
USPC ...................... 514/23, 315; 546/242; 435/184
See application file for complete search history.

(56) References Cited

U.S. PATENT DOCUMENTS 6,489,317 B1 * 12/2002 Borody .................. 514/197

FOREIGN PATENT DOCUMENTS

WO WO03002127 A1 * 1/2003

OTHER PUBLICATIONS

Dubernet et. al., Bioorganic and Medicinal Chemistry Letters, 2006, Elsevier, vol. 16, pp. 1172-1174.*
http://www.medicinenet.com/helicobacter_pylori/page7.htm.*
Zavala-Spinetti et. al., Helicobacter, 2006, Blackwell Publishing Ltd, vol. 11, pp. 517-522.*

* cited by examiner

*Primary Examiner* — Sarah Pihonak
(74) *Attorney, Agent, or Firm* — Wolf, Greenfield & Sacks, P.C.

(57) ABSTRACT

Methods of diagnosing *Helicobacter pylori* infection or associated conditions are based in part on the correlation of the presence of a α-L-fucosidase 2 marker with the infection. Methods and compositions for treating or preventing *Helicobacter pylori* infection or associated conditions are based in part on administering an α-L-fucosidase 2 inhibitor to an infected subject or a subject at risk of developing the infection.

5 Claims, 19 Drawing Sheets

(5 of 19 Drawing Sheet(s) Filed in Color)

FIG. 5

```
FUCA2  MRPQELP-RLAFPLLLLLLLLLPPPPCP--AHSATRFDPTWESLDARQLR    47
FUCA1  --APGMRS-P-G-A------F-GAAESVRR-QPPRRYT-D-P---S-P--    50

FUCA2  AWPDQAKFGIFIHWGVFSVPSFGSEWFWWYWQKEKIPKYVEFMKDNYPPS    97
FUCA1  ----E----V----------AW-------H--G-GR-Q-QR--R-----G   100

FUCA2  FKYEDRGPLYSAKFFNANQWADIFQASGAKYIVLTSKHHEGFTLWGSEYS   147
FUCA1  -S-A----Q---R--HPEE---L---A----V---T-------N-P-PV-   150

FUCA2  WNWNAIDEGPKRDIVKELEVAIRNRTDLRFGLYYSLFEWFHPLFLEDESS   197
FUCA1  ----SK-V--H--L-G--GT-L-K- NI-Y---H--L------Y-L-KKN   199

FUCA2  SFHKRQFPVSKTLPELYELVNNYQPEVLWSDGDGGAPDQYWNSTGFLAWL   247
FUCA1  G-KTQH-VSA--M----D---S-K-DLI----EWEC--T-----N--S--   249

FUCA2  YNESPVRGTVVTNDRWGAGSICKHGGFYTCSDRYNPGHLLPHKWENCMTI   297
FUCA1  --D---KDE--V-----QNCS-H---Y-N-E-KFK-QS-PD----M-TS-   299

FUCA2  DKLSWGYRREAGISDYLTIEELVKQLVETVSCGGNLLMNIGPTLDGTISV   347
FUCA1  --F------DMAL--VTEES-IISE--QTVSL---Y-L------K--L-VP  349

FUCA2  VFEERLRQVGSWLKVNGEAIYETYTWRSQNDTVTPDVWYTSKPKEKLVYA   397
FUCA1  I-Q---LA--K--SI------ASKP--V-WEKN-TS------ GSA---   397

FUCA2  IFLKWPTSGQLFLGHPKAILGATEVKLLGHGQPLNWISLEQNGIMVELPQ   447  (SEQ. ID No: 3)
FUCA1  ---H--EN-V-N-ES-ITTS-T-KITM--IQGD-K-STDPDK-LFIS---   446  (SEQ. ID No: 4)
```

COMPOSITIONS AND ASSAYS FOR TREATMENT AND DIAGNOSIS OF HELICOBACTER PYLORI INFECTION AND CONDITIONS

CROSS-REFERENCE TO RELATED APPLICATIONS

The present application is a non-provisional of U.S. Provisional Application 61/230,674, filed on Jul. 31, 2009.

BACKGROUND

1. Field

Aspects of the invention relate to devices and related methods of diagnosing conditions associated with the presence of *Helicobacter pylori* (*H. pylori*) in a biological sample, and compositions and related methods for treating *Helicobacter pylori* caused conditions. α-L-fucosidase 2 may be used as a diagnostic marker and a therapeutic target for *H. pylori* related diseases.

2. Description of the Related Art

About one-half of the global human population is currently infected with *Helicobacter pylori*, which mainly colonizes the gastric mucosa. Although this pathogen is a leading cause of gastric malignancies (Peek, et. al., *Nat. Rev. Cancer* 2002, 2:28-37; Cave, D. R. *Gastrointest. Dis.* 2001, 12:196-202; Sipponen, et. al., *Scand. J. Gastroenterol. Suppl.* 1993, 196: 3-6), most infected individuals remain asymptomatic or are affected merely by chronic gastritis (Cave, D. R. *Gastrointest. Dis.* 2001, 12:196-202). About 20% of infected patients develop peptic ulcer, gastric cancer, or malignant lymphoma, revealing potential host defense mechanisms against *H. pylori* pathogenesis.

As a first step for successful infection, *H. pylori* adheres to the gastric mucosa of epithelial cells. The microbial and host factors that determine the outcome of colonization have been difficult to define, however, in part because of the genetic diversity among *H. pylori* strains and among humans. The infection process may rely on the pathogen to establish physical contact with the gastric epithelium through *H. pylori* adhesins. The *H. pylori* strains that harbor the gene babA2, which encodes the adhesin BabA, are associated with an increased risk for gastric adenocarcinoma (Gerhard, et al., *Proc. Natl. Acad. Sci. USA* 1999, 96:12778-12783). In addition, SabA was identified as a sialic acid-binding adhesin that binds several sialylated glycoconjugates, including the tetrasaccharide sialyl Lewis X (sialyl Le$^x$), expressed on gastric mucins during chronic *H. pylori*-mediated inflammation (Mandavi, et al., *Science* 2002, 297:573-578). The expression of sialyl Le$^x$ in gastric epithelium is induced during persistent *H. pylori* infection, suggesting that *H. pylori* may trigger the host tissue to modify the gastric mucosal glycosylation patterns to express the ligands for bacterial adhesins.

The work done by Gordon and coworkers (Hooper, et al., *Proc. Natl. Acad. Sci. USA* 1999, 96:9833-9838) demonstrated that *Bacteroides thetaiotaomicron*, a commensal bacterium of the distal small intestine, can induce host synthesis of a specific glycan structure that the microbe can then utilize as a supply of L-fucose residues. L-Fucose is hydrolytically removed and utilized by the bacteria as a carbon and energy source. Thus, it would be helpful to the art to determine whether L-fucose plays a similar role in the interaction between *H. pylori* and gastric epithelial cells. A recent study showed that *H. pylori* induced host cells to overexpress β1,3-N-acetylglucosaminyltransferase (β3GnT5), which indirectly produced more sialyl Le$^x$ (Marcos, et al., *J. Clin. Invest.* 2008, 118:2325-2336), suggesting that the pathogen may induce the host to manufacture specific glycans and to activate transcription of several genes simultaneously.

Although *H. pylori* is well established as the primary cause of gastritis, duodenal ulcer and gastric cancer, currently there is no clear information regarding if and how host cells interact with *H. pylori* and if such interactions are dependent on the type of gastric disease.

SUMMARY

α-L-fucosidase 2 (FUCA2) mediates L-fucose transferred from the surface of human gastric cancer cells to the co-cultured clinical strain of *H. pylori*. This discovery enables development methods for the diagnosis of *H. pylori*. Some methods may comprise determining the presence of an α-L-fucosidase 2 in a biological sample. Some aspects of the present invention also provide compositions and methods for the prevention or treatment of conditions associated with *Helicobacter pylori* infection. Compositions may comprise an α-L-fucosidase 2 inhibitor, its pharmacologically acceptable salt, ester, amide, hydrate or solvate. Methods may comprise administering to a subject in need thereof, a therapeutically effective amount of an □-L-fucosidase 2 inhibitor, its pharmacologically acceptable salt, ester, amide, hydrate or solvate.

In some embodiments, a pharmaceutical composition comprises a therapeutically effective amount of α-L-fucosidase 2 inhibitor, its pharmacologically acceptable salt, ester, amide, hydrate or solvate; and a pharmaceutically acceptable carrier, excipient or diluent; wherein the pharmaceutical composition is formulated to target the gastric epithelium of a subject; and wherein the pharmaceutical composition is formulated to prevent or disrupt adhesion of *Helicobacter pylori* to the gastric epithelium. Some α-L-fucosidase 2 inhibitors are known in the art and include fuconojirimycin, a fuconojirimycin analog, or a pharmacologically acceptable salt, ester, or amide thereof. A fuconojirimycin analog may have the structure of formula:

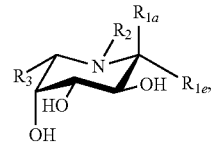

wherein $R_{1a}$, $R_{1e}$, $R_2$ and $R_3$ are independently H, alkyl, alkenyl, alkynyl, acyl, aryl, arylalkyl, or arylacyl, or the heteroatom forms of the foregoing, wherein the fuconojirimycin analog is unsubstituted or substituted with a substituent that will not affect the inhibition of α-L-fucosidase 2, or a pharmacologically acceptable salt, ester, or amide thereof, such as 1-deoxy-fuconojirimycin, or a pharmacologically acceptable salt, ester, or amide thereof. Combinations are also contemplated. For example, a combination may comprise at least one α-L-fucosidase 2 inhibitor with one or more of a proton pump inhibitor, H$_2$-receptor antagonist, and/or one or more antibiotics. One combination may include a α-L-fucosidase 2 inhibitor, one, two or three antibiotics and a proton pump inhibitor. The composition may be formulated for oral administration.

In another embodiment, a method of treating a *Helicobacter pylori* infection comprises administering to a subject in need thereof the composition described herein. A method of treating a *Helicobacter pylori* infection may also comprise selecting a subject infected with *Helicobacter pylori*; and administering to the subject, a therapeutically effective amount of an α-L-fucosidase 2 inhibitor, its pharmacologically acceptable salt, ester, amide, hydrate or solvate wherein the *Helicobacter pylori* infection is treated upon the administering step. In some cases, the subject has a condition such as one selected from the group consisting of chronic superficial gastritis, gastric ulcer, duodenal ulcer, gastric adenocarcinoma, non-Hodgkin lymphoma in human stomach, liver disease, colorectal disease, pancreatic disease, skin disease, heart disease, and autoimmune diseases. Examples of autoimmune diseases include autoimmune gastritis, pernicious anemia or non-steroid anti-inflammatory drug (NSAID) related gastric disease.

In another embodiment, a method of preventing *Helicobacter pylori* infection comprises selecting a subject that is not infected with *Helicobacter pylori*; and administering to the subject, a therapeutically effective amount of an α-L-fucosidase 2 inhibitor, its pharmacologically to acceptable salt, ester, amide, hydrate or solvate thereof that prevents *Helicobacter pylori* infection.

A marker may include an α-L-fucosidase 2 fragment that differs from α-L-fucosidase 1 such as the sequence $^{100}$YEDFGPLFTAK$^{110}$ (SEQ ID NO. 1) or $^{45}$QLPAWFFQ$^{52}$ (SEQ ID NO. 2).

A kit for the diagnosis of a *Helicobacter pylori* infection in a subject may comprise a compound that selectively binds to a polypeptide comprising an α-L-fucosidase 2 fragment described herein and instructions for use.

Detection methods are also contemplated. A method of detecting *Helicobacter pylori* infection in a biological sample from a subject suspected of having *Helicobacter pylori* infection, may comprise determining the presence of a polypeptide comprising the α-L-fucosidase 2 fragment described herein in the biological sample, wherein the presence of the polypeptide is indicative of the presence of *Helicobacter pylori* in the subject. The polypeptided detected may be $^{100}$YEDFGPLFTAK$^{110}$ (SEQ ID NO. 1) or $^{45}$QLPAWFFQ$^{52}$ (SEQ ID NO. 2), which may be detected by a mass spectrometer.

An assay for the diagnosis of a *Helicobacter pylori* infection in a subject comprises a compound that detects the presence of a polypeptide comprising an α-L-fucosidase 2 fragment that differs from a corresponding fragment of α-L-fucosidase 1, such as an immunoassay, a biochip array or an enzyme activity assay.

These and other embodiments are described in greater detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A shows the measurement of α-L-fucosidase activity which was carried out with *H. pylori* alone (●), Capan 1 alone (▽), or the co-culture (■) of Capan 1 and *H. pylori* (MOI ~200:1). α-L-Fucosidase from *Corynebacterium* sp. was used as a positive control (◇). Furthermore, the activity of the secreted α-L-fucosidases by five gastric cancer cell lines was measured either in the absence (4B) or presence (4C) of *H. pylori* (MOI ~200:1).

FIG. 5 is a sequence alignment of human α-L-fucosidase 1 (FUCA1, SEQ ID NO: 4) and α-L-fucosidase 2 (FUCA2, SEQ ID NO: 3). Two peptide fragments $^{100}$YEDFGPLFTAK$^{110}$ (SEQ ID NO. 1) and $^{45}$QLPAWFFQ$^{52}$ (SEQ ID NO. 2)) identified by MS/MS are shaded in gray. Dashes indicate amino acid residues of FUCA1 and FUCA2 that are identical.

(FIG. 7a) Both mock-transfected Capan 1 cells and Capan 1-FUCA2 K.D. cells were infected with a comparable number of H. pylori, and doubly stained with anti-H. pylori (Alexa Fluor 488, green) and a nuclei-specific dye (DAPI, red). After 8 h of co-culturing, the number of adherent H. pylori was reduced to ~50% in Capan 1-FUCA2 K.D. cells. Phase-contrast photographs indicate the same field. (7b, 7c) Immunoblot analysis of epithelial cells infected with H. pylori using mouse monoclonal anti-CagA. Both mock-transfected Capan 1 (7b) and Capan 1-FUCA2 K.D. cells (7c) were infected with different H. pylori strains, including CagA$^+$ and CagA$^-$, and various clinical isolates from patients with gastritis (GS), duodenal ulcer (DU) and gastric cancer (GC). PBS represents the negative control. The co-culture was maintained for 6-8 h at an MOI of ~200:1. CagA (~140 kDa) was detected when the mock-transfected Capan 1 cells were infected with various strains of H. pylori, except for the CagA$^-$ strain (7b). In contrast, CagA was not detected in Capan 1-FUCA2 K.D. H. pylori-infected cells with the exception of GS (7c).

DETAILED DESCRIPTION OF THE PREFERRED EMBODIMENT

Figure 1:
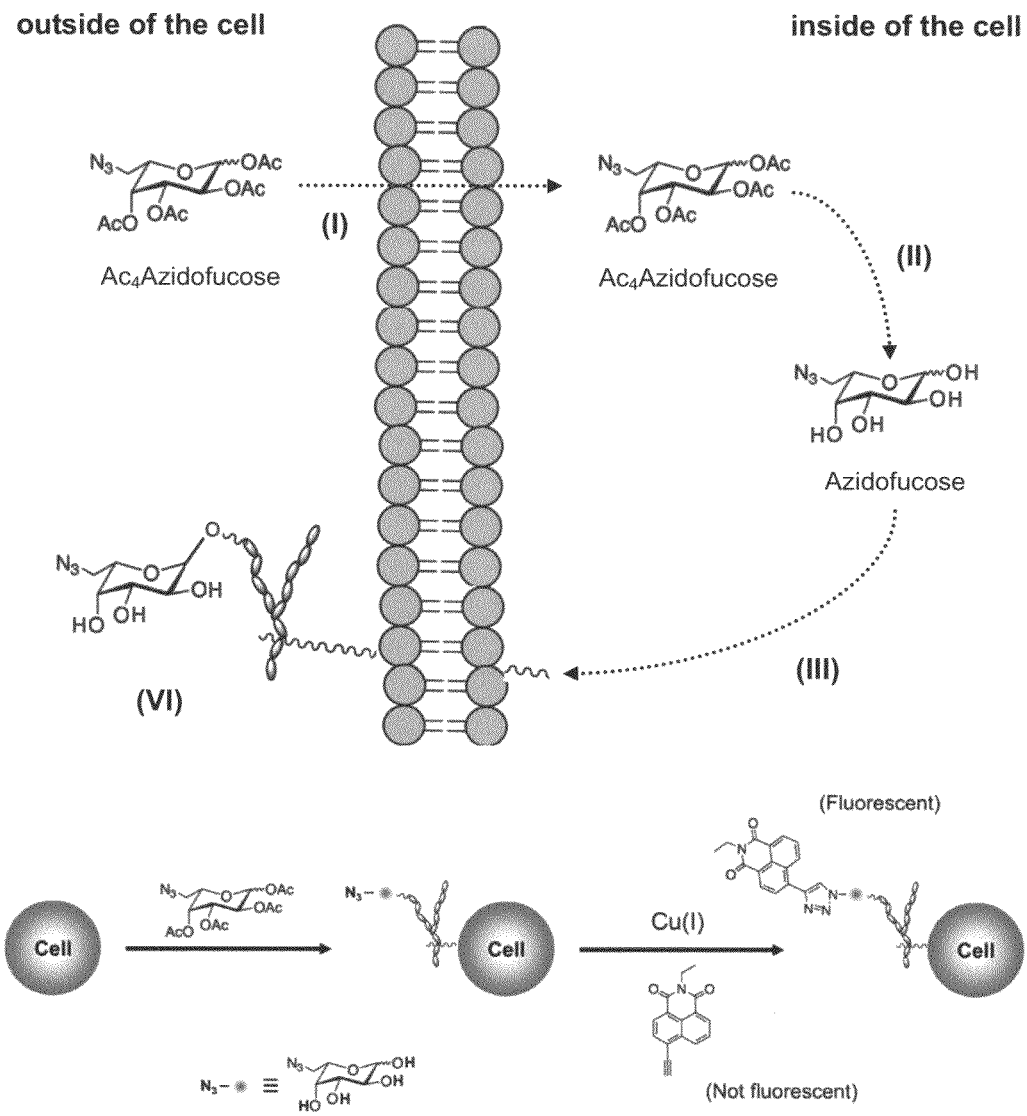
FIG. 1 provides a schematic representation showing metabolic incorporation of tetra-O-acetyl-6-azido-L-fucose, including (I) diffusion of the sugar probe into the cell; (II) hydrolysis of the acetyl groups of the sugar probe by nonspecific esterases; (III) incorporation of azidofucose into the L-fucose-related biosynthetic pathway; (IV) presentation of 6-azido-L-fucose-containing glycans on the cell surface. After 6-azido-L-fucose was incorporated into glycans, 4-ethynyl-N-ethyl-1,8-naphthalimide (non-fluorescent) was reacted with the azide group by a Cu(I)-catalyzed [3+2] cycloaddition reaction to generate the fluorescent adduct.

Aspects of the present invention provide methods of diagnosing a condition associated with the presence of Helicobacter pylori in a biological sample, comprising determining the presence in said sample of an α-L-fucosidase 2 (FUCA2). It was determined that FUCA2 is secreted by H. pylori-infected gastric cancer (GC) cells but not by individual cultures of H. pylori or GC cells. Thus the presence of FUCA2 in a sample is indicative of a condition associated with the presence of H. pylori.

As used herein, a "condition" associated with the presence of H. pylori refers to such condition as chronic superficial gastritis, gastric ulcer, duodenal ulcer, gastric adenocarcinoma, non-Hodgkin lymphoma in human stomach, liver disease, pancreatic disease, skin disease, heart disease, and autoimmune diseases such as autoimmune gastritis, pernicious anaemia or non-steroid anti-inflammatory drug (NSAID) related gastric disease, and the like.

In certain embodiments, the determining step can be carried out, for example, by detecting the presence of markers such as $^{100}$YEDFGPLFTAK$^{110}$ peptide (SEQ ID NO. 1) or $^{45}$QLPAWFFQ$^{52}$ peptide (SEQ ID NO. 2) as an indication of the presence of alpha-L-fucosidase 2 marker in a sample. The detection may be carried out by a mass spectrometer, preferably by a tandem mass spectrometer. The $^{100}$YEDFGPLFTAK$^{110}$ peptide (SEQ ID NO. 1) and $^{45}$QLPAWFFQ$^{52}$ peptide (SEQ ID NO. 2), unique to FUCA 2, may be present as fragment ions in the MS spectrum of a doubly charged ion about m/z 624 and 518 respectively.

The detection of the presence of $^{100}$YEDFGPLFTAK$^{110}$ peptide (SEQ ID NO. 1) or $^{45}$QLPAWFFQ$^{52}$ peptide (SEQ ID NO. 2) may be carried out, for example, by other suitable methods as can readily be identified by a person skilled in the art. For example, known peptide detection methods or assays such as detection of angiotensin I peptide could be adapted to detect the presence of $^{100}$YEDFGPLFTAK$^{110}$ peptide (SEQ ID NO. 1).

In addition, any fragment of α-L-fucosidase 2, or peptide comprising such a fragment, that differs from a corresponding fragment of α-L-fucosidase 1 can serve as a marker in the peptide detection method or assay. One skilled in the art would be able to determine the appropriate fragment, for example, by comparing the sequence shown in FIG. 5, and determining which portion of the α-L-fucosidase 2 contains at least one different amino acid relative to the α-L-fucosidase 1 sequence. The longest stretch of consecutive amino acids that are identical in both sequences in FIG. 5 (as shown by dashes) is 10 amino acids in length, therefore, in some aspects, the peptide to be detected should include at least 11 consecutive amino acids from α-L-fucosidase 2. However, peptides comprising shorter fragments containing less than 11 consecutive amino acids are also contemplated such as a fragment having 8 consecutive amino acids such as $^{45}$QLPAWFFQ$^{52}$ peptide (SEQ ID NO. 2). In some aspects, a fragment may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 (and so on) or more amino acids in length.

In other embodiments, there are provided kits for the diagnosis of a condition associated with the presence of *Helicobacter pylori* comprising an antibody that binds α-L-fucosidase 2 and reagents for detecting immunological type reactions of α-L-fucosidase 2-antibody complex. For example, an α-L-fucosidase antibody, such as anti-(human alpha-L-fucosidase) antibody, could be used in a kit along with p-nitrophenyl-α-L-focoside as substrate for a sandwich type immunological reaction to determine the presence of α-L-fucosidase 2 that is indicative of *Helicobacter pylori*. Other possible methods to detect the presence of FUCA2 include enzyme activity assay (e.g. a chromogenic substrate or fluorescence-generating substrate) and inhibitor-based affinity chromatography.

FUCA2 affects *H. pylori* adhesion to gastric epithelial cells and regulates the level of Le$^x$ antigen at the same time. The two results are apparently correlated with each other. As known in the art, *H. pylori* strains strongly expressing sialyl Lewis x/y (Le$^{x/y}$) are linked to higher-density colonization, as compared to strains that weakly produce Le$^{x/y}$ (Heneghan, et al., Infect. Immun. 2000, 68:937-941). The pathogen thus likely evolves to develop various countermeasures against the host defense, suggesting an opposing interplay between *H. pylori* and the host.

The effect of FUCA2 on *H. pylori* was also examined by two studies: RNA interference-mediated depletion of FUCA2 and treatment of *H. pylori*-infected cells with fuconojirimycin (FNJ), both of which effectively prevented adherence of *H. pylori* to host cells and significantly reduced the level of Le$^x$-containing glycoproteins in *H. pylori*.

The adhesion of *H. pylori* to host cells is likely mediated by C-type lectins found on the surface mucous cells of the gastric pit (Cambi, et al., *Cell. Microbiol.* 2005, 7:481-488). Bacterial adhesion to host cells is an important initial event in the pathogenesis of gastric malignancies, and inhibition of bacterial adhesion may prevent certain pathogen-related diseases, such as duodenal ulcers (DU) and gastric cancer (GC). The current eradication strategy requires a combination of one, two, or three antibiotics and a proton pump inhibitor (Unge P. *Curr. Top. Microbiol. Immunol.* 1999, 241:261-300). H$_2$-receptor antagonists may be used to substitute proton pump inhibitors. In some aspects, a combination is contemplated cotaining alpha-L-fucosidase 2 inhibitor, its pharmacologically acceptable salt, ester, amide, or a hydrate or solvate; one, two, or three antibiotics, and/or a proton pump inhibitor and/or an H$_2$-receptor antagonists.

For example, antibiotics used to treat *H. pylori* infection include amoxicillin (β-lactam antibiotics), clarithromycin (macrolide antibiotics), metronidazole, tetracycline and other antibiotics suitable for use to treat *H. pylori* infection.

Proton pump inhibitor decreases the stomach's production of acid, which allows the tissues damaged by the infection to heal. Examples of proton pump inhibitors include lansoprazole (Prevacid®), omeprazole (Prilosec®), pantoprazole (Protonix®), rabeprazole (AcipHex®) and esomeprazole (Nexium®).

H2-receptor antagonists have similar effects as proton pump inhibitors but with different mode of action. For example, cimetidine, ranitidine, famotidine and nizatidine are commonly used in US.

Due to ever-increasing concerns about antibiotic resistance (Glupczynski Y. *Acta Gastroenterol. Belg.* 1998, 61:357-366), the lack of protection against re-infection, the necessity of taking a long-term prescription for complete eradication, and the high cost of therapy, other therapeutic alternatives described herein would be of interest.

In some embodiments, the present invention provides methods for the prevention or treatment of a condition associated with the presence of *Helicobacter pylori*, comprising administering to a subject in need thereof, a therapeutically effective amount of an alpha-L-fucosidase 2 inhibitor, its pharmacologically acceptable salt, ester, amide, or a hydrate or solvate. Fuconojirimycin and fuconojirimycin analogues can be made as any pharmacologically acceptable salt, ester, amide, hydrate or solvate. For example, they can be accompanied with chloride, sulfate, phosphate, or sulfonate (negative ions). In addition, each of these molecules was found to have 1-4 hydrates or ethanols, depending on the preparation conditions. The condition to be treated may be caused by the presence of *H. pylori* in the gastrointestinal tract of the subject. The condition may be selected from the group consisting of chronic superficial gastritis, gastric ulcer, duodenal ulcer, gastric adenocarcinoma, non-Hodgkin lymphoma in human stomach, liver disease, pancreatic disease, skin disease, colorectal disease, heart disease, and autoimmune diseases. The autoimmune disease may be autoimmune gastritis, pernicious anemia or non-steroid anti-inflammatory drug (NSAID) related gastric disease.

As used herein, the term "treatment" refers to (1) preventing the disease or infection from occurring in a patient that is predisposed or does not yet display symptoms of the disease or infection; (2) inhibiting the disease or infection or arresting its development; or (3) ameliorating or causing regression of the disease or infection. The treatment may be either performed in an acute or in a chronic way.

In some embodiments, the α-L-fucosidase 2 inhibitor may be a fucopyranosylamine analog, a 1,5-dideoxy-1,5-imino-L-talitol analog, a fuconojirimycin analog, and the like; preferably 1-deoxy-fuconojirimycin.

As used herein, the term "fuconojirimycin analog" refers to a compound that inhibits α-L-fucosidase 2 that is structurally related to fuconojirimycin, such as a fuconojirimycin analog having the following formula:

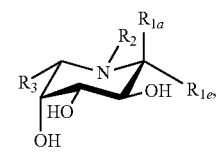

wherein R$_1$a, R$_1$e, R$_2$ and R$_3$ are independently H, alkyl, alkenyl, alkynyl, acyl, aryl, arylalkyl, or arylacyl, or the heteroatom forms of the foregoing, optionally substituted with a substituent that will not affect the inhibition of α-L-fucosidase 2, e.g., 1-deoxy-fuconojirimycin (R$_1$a, R$_1$e, R$_2$:H; R$_3$: methyl). For fuconojirimycin, either R$_1$a, or R$_1$e is a hydroxyl group (both isomers quickly interconvert to each other), R$_2$ is H and $R_3$ is a methyl group. In some embodiments, $R_1a$, $R_1e$, $R_2$ and $R_3$ are independently H or alkyl; such as 1-6C alkyl.

Any substituent that leaves the ability of the "fuconojirimycin analog" to inhibit α-L-fucosidase 2 is suitable. A wide variety of substituents can be employed in these positions, and it is well within ordinary skill to determine any particular substituent will affect the inhibition of α-L-fucosidase 2. See Ho et al., Biochemistry 2006, 45, 5495-5702.

As used herein, the term "alkyl," "alkenyl" and "alkynyl" include straight- and branched-chain and cyclic monovalent substituents. Examples include methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—), cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Heteroalkyl, heteroalkenyl and heteroalkynyl are similarly defined but may contain 1-2O, S or N heteroatoms or combinations thereof within the backbone residue.

As used herein, "hydrocarbyl residue" refers to a residue that contains only carbon and hydrogen. The residue may be aliphatic or aromatic, straight-chain, cyclic, branched, saturated or unsaturated. The hydrocarbyl residue, when so stated however, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or may contain heteroatoms within the "backbone" of the hydrocarbyl residue.

"Aromatic" moiety, "aryl" and "Ar" refer to a monocyclic or fused bicyclic moiety such as phenyl, naphthyl, or anthryl including those that contain one or more heteroatoms; "heteroaromatic" itself refers to monocyclic or fused bicyclic ring systems containing one or more heteroatoms selected from O, S and N, such as 1 to 4 heteroatoms. The inclusion of a heteroatom permits inclusion of 5-membered rings as well as 6-membered rings. Thus, typical aromatic systems include phenyl, naphthyl, pyridyl, pyrimidyl, pyridinyl, thiadiazolyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl, indolizinyl, benzothienyl, thiadiazolyl and the like. The nitrogen and/or the sulfur ring atom(s) of the heteroaryl group may be optionally oxidized to provide for the N-oxide (N→O), sulfinyl, or sulfonyl moieties. Any monocyclic or fused ring bicyclic system which has the characteristics of aromaticity in terms of electron distribution throughout the ring system is included in this definition. Typically, the ring systems contain 5-12 ring member atoms, and/or 1 to 10 or 6 to 14 carbon atoms. Condensed rings may or may not be aromatic (e.g., 2-benzoxazolinone, 2H-1,4-benzoxazin-3(4H)-one-7-yl, and the like) provided that the point of attachment is at an aromatic carbon atom.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide these substituents as acyl moieties.

As used herein, "acyl" encompasses the definitions of alkyl, alkenyl, alkynyl and the related hetero-forms which are coupled to an additional residue through a carbonyl group.

Each substituent on Ar is independently a hydrocarbyl residue (1-20C) containing 0-5 heteroatoms selected from O, S and N, or is an inorganic residue. As used herein, "inorganic residue" refers to a residue that does not contain carbon. Examples include, but are not limited to, halo, hydroxy, $NO_2$ or $NH_2$. Exemplary substituents include those selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, arylacyl, heteroarylacyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_{22}$, $SO_2NR_{22}$, $NRSO_2NR_2$, CN, $CF_3$, $R_3Si$, and $NO_2$, wherein each R is independently H, alkyl, alkenyl or aryl or heteroforms thereof, and wherein two of said optional substituents on adjacent positions can be joined to form a fused, optionally substituted aromatic or nonaromatic, saturated or unsaturated ring which contains 3-8 members. Other substituents may include halo, alkyl (1-4C), alkoxy (1-6C) and more preferably, fluoro, chloro and methyl. These substituents may occupy all available positions of the aryl ring, preferably 1-2 positions, most preferably one position or Ar may be unsubstituted. These substituents may be optionally substituted with substituents similar to those listed. Of course some substituents, such as halo, are not further substituted, as known to one skilled in the art.

When an α-L-fucosidase 2 inhibitor contains one or more chiral centers, the invention includes optically pure forms as well as mixtures of stereoisomers or enantiomers.

In certain embodiments, the methods for the prevention or treatment of a condition associated with the presence of *Helicobacter pylori*, further comprise administering to a subject in need thereof, a therapeutically effective amount of a proton pump inhibitor, its pharmacologically acceptable salt, ester, amide, hydrate or solvate. In related embodiments, the methods further comprise one or more antibiotics, e.g. β-lactam antibiotics, macrolide antibiotics, metronidazoles, tetracyclines, and other antibiotics suitable for use to treat *H. pylori* infection.

In yet other embodiments, compositions are provided for the prevention or treatment of a condition associated with the presence of *Helicobacter pylori*, said composition comprising an α-L-fucosidase 2 inhibitor, its pharmacologically acceptable salt, or a hydrate or solvate and a pharmaceutically acceptable carrier. The condition may be selected from the group consisting of chronic superficial gastritis, gastric ulcer, duodenal ulcer, gastric adenocarcinoma, non-Hodgkin lymphoma in human stomach, liver disease, pancreatic disease, skin disease, colorectal disease, heart disease, autoimmune diseases, and the like. The autoimmune disease may be autoimmune gastritis, pernicious anaemia or non-steroid anti-inflammatory drug (NSAID) related gastric disease. The composition may further comprise a proton pump inhibitor and/or one or more antibiotics suitable for use to treat *H. pylori* infection.

As used herein, the term "pharmacologically acceptable salt" includes salts of acidic or basic groups that may be present in compounds used herein. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included, in the present compositions that include an amino moiety may form pharmaceutically acceptable salts with various amino acids, in addition to the acids mentioned above. Compounds, which are acidic in nature, are capable of forming base salts with various pharmacologically acceptable cations. Examples of such salts include alkali metal or alkaline earth metal salts and, particularly, calcium, magnesium, sodium lithium, zinc, potassium, and iron salts. For example, pharmaceutically acceptable salts have been compiled in P. Heinrich Stahl and Camille G. Wermuth, Handbook of Pharmaceutical Salts: Properties, Selection and Use. International Union of Pure and Applied Chemistry, Wiley-VCH 2002, and L. D. Bighley, S. M. Berge, D. C. Monkhouse, in "Encyclopedia of Pharmaceutical Technology". Eds. J. Swarbrick and J. C. Boylan, Vol. 13, Marcel Dekker, Inc., New York, Basel, Hong Kong 1995, pp. 453-499.

Those skilled in the art will appreciate that a variety of prodrugs, salts, esters, amides, hydrates, solvates, and polymorphs can be produced from the compounds disclosed here, and that various isotopically-substituted variants (through, e.g., substitution of deuterium for hydrogen, $^{13}C$ for carbon, $^{15}N$ for nitrogen, or $^{32}P$ for phosphorus) can also be readily produced. All such derivatives are contemplated within the scope of this disclosure.

In other aspects, the present disclosure relates to a pharmaceutical composition comprising an α-L-fucosidase 2 inhibitor and one or more components that allow the α-L-fucosidase 2 inhibitor to target the gastric epithelium. It is well within the skill in the art to formulate a composition that targets a particular site within the body to provide effective pharmacological action. See Remington's Pharmaceutical Sciences, 18th Ed., Mack Publishing Co., Easton, Pa. (1990), which is incorporated herein by reference in its entirety. In some aspects, useful components that target the gastric epithelium neutralize gastric acidity and/or inhibit acid secretion. See, e.g., U.S. Pat. No. 5,593,696. Gastric neutralizers or buffers such as sodium carbonate or sodium bicarbonate may be useful in formulating compositions described herein.

Other additional components may be included as well such as physiologically acceptable surface active agents, additional carriers, diluents, excipients, smoothing agents, suspension agents, film forming substances, and coating assistants, or a combination thereof. Acceptable additional carriers or diluents for therapeutic use are well known in the pharmaceutical art, and are described, for example, in Remington's Pharmaceutical Sciences, 18th Ed., Mack Publishing Co., Easton, Pa. (1990. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical composition facilitates administration of the compound to an organism. Multiple techniques of administering a pharmaceutical composition exist in the art including, but not limited to, oral. In some embodiments, pharmaceutically acceptable salts of the compounds disclosed herein are provided.

The term "carrier" includes a chemical compound that facilitates the targeting of the inhibitor to the cells or tissues of interest.

The term "diluent" includes chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds described herein can be administered to a human patient per se, or in pharmaceutical compositions where they are mixed with other active ingredients, as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of the α-L-fucosidase 2 inhibitor for treatment or prevention of the infection and/or condition as part of a particular administration protocol, as would be understood by those of skill in the art. Techniques for formulation and administration of the compounds of the instant application may be found in "Remington's Pharmaceutical Sciences," Mack Publishing Co., Easton, Pa., 18th edition, 1990.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Actual dosage levels of the active ingredients in the compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion of the particular compositions being employed, the duration of the treatment, other drugs, compounds and/or materials used in combination with the particular therapeutic employed, the age, sex, weight, condition, general health and prior medical history of the patient being treated, and like factors well known in the medical arts.

In general, a suitable daily dose of a compound will be that amount of the compound which is the lowest dose effective to produce a therapeutic effect. Such an effective dose will generally depend upon the factors described above.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In cases of administration of a pharmaceutically acceptable salt, dosages may be calculated as the free acid. In some embodiments, the composition is administered 1 to 4 times per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In some embodiments, in the pharmaceutical industry, it standard practice to provide substantially pure material when formulating pharmaceutical compositions. Therefore, in some embodiments, "substantially pure" refers to the amount of purity required for formulating pharmaceuticals, which may include, for example, a small amount of amorphous material or other material, wherein the material may still achieve sufficient pourability, lack of hygroscopicity, and purity suitable for pharmaceutical use. In some embodiments, the substantially pure compound contains at least about 96% of the compound by weight, such as at least about 97%, 98%, 99%, or 100% of the compound.

The compositions according to some embodiments of the present invention may be administered to humans and other animals for therapy as either a single dose or in multiple doses. The compositions may be administered either as individual therapeutic agents or in combination with other therapeutic agents. The treatments may be combined with conventional therapies, which may be administered sequentially or simultaneously. In some embodiments, routes of administration include those selected from the group consisting of oral and local administration, and the like.

For oral administration, the composition can be formulated readily by combining the compositions of interest with pharmaceutically acceptable carriers well known in the art. Such carriers enable the compositions of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Pharmaceutical compositions suitable for administration include compositions where the active ingredients are contained in an amount effective to achieve its intended purpose. In some embodiments, a therapeutically effective amount of a compound is an amount effective to treat a bacterial infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are about 0.1% to about 500%, more preferably about 25% to about 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

"Marker" as used herein has its ordinary meaning as known to those skilled in the art and refers to a polypeptide that is differentially present in a sample taken from subjects with a *Helicobacter pylori* infection as compared to a comparable sample taken from control subjects (e.g., a subject with a negative diagnosis, normal or healthy subject).

"Diagnostic" as used herein has its ordinary meaning as known to those skilled in the art and refers to identifying the presence of a pathologic condition wherein a positive indication that aids in diagnosis *Helicobacter pylori* infection.

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "subject," "patient" or "individual" as used herein has its ordinary meaning as known to those skilled in the art and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

"Ameliorated" or "treatment" as used herein has its ordinary meaning as known to those skilled in the art and refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

"Probe" as used herein has its ordinary meaning as known to those skilled in the art and refers to a device that is removably insertable into a gas phase ion spectrometer and comprises a substrate having a surface for presenting a marker for detection. A probe can comprise a single substrate or a plurality of substrates.

"Substrate" or "probe substrate" as used herein has its ordinary meaning as known to those skilled in the art and refers to a solid phase onto which an adsorbent can be provided (e.g., by attachment, deposition, etc.).

"Adsorbent" as used herein has its ordinary meaning as known to those skilled in the art and refers to any material capable of adsorbing a marker. The term "adsorbent" is used herein to refer both to a single material ("monoplex adsorbent") (e.g., a compound or functional group) to which the marker is exposed, and to a plurality of different materials ("multiplex adsorbent") to which the marker is exposed. The adsorbent materials in a multiplex adsorbent are referred to as "adsorbent species." For example, an addressable location on a probe substrate can comprise a multiplex adsorbent characterized by many different adsorbent species (e.g., anion exchange materials, metal chelators, or antibodies), having different binding characteristics. Substrate material itself can also contribute to adsorbing a marker and may be considered part of an "adsorbent."

"Adsorption" or "retention" as used herein has its ordinary meaning as known to those skilled in the art and refers to the detectable binding between an absorbent and a marker either before or after washing with an eluant (selectivity threshold modifier) or a washing solution.

"Eluant" or "washing solution" as used herein has its ordinary meaning as known to those skilled in the art and refers to an agent that can be used to mediate adsorption of a marker to an adsorbent. Eluants and washing solutions are also referred to as "selectivity threshold modifiers." Eluants and washing solutions can be used to wash and remove unbound materials from the probe substrate surface.

"Resolve," "resolution," or "resolution of marker" as used herein has its ordinary meaning as known to those skilled in the art and refers to the detection of at least one marker in a sample. Resolution includes the detection of a plurality of markers in a sample by separation and subsequent differential detection. Resolution does not require the complete separation of one or more markers from all other biomolecules in a mixture. Rather, any separation that allows the distinction between at least one marker and other biomolecules suffices.

"Gas phase ion spectrometer" as used herein has its ordinary meaning as known to those skilled in the art and refers to an apparatus that measures a parameter which can be translated into mass-to-charge ratios of ions formed when a sample is volatilized and ionized. Generally ions of interest bear a single charge, and mass-to-charge ratios are often simply referred to as mass. Gas phase ion spectrometers include, for example, mass spectrometers, ion mobility spectrometers, and total ion current measuring devices.

"Mass spectrometer" as used herein has its ordinary meaning as known to those skilled in the art and refers to a gas phase ion spectrometer that includes an inlet system, an ionization source, an ion optic assembly, a mass analyzer, and a detector.

"Laser desorption mass spectrometer" as used herein has its ordinary meaning as known to those skilled in the art and refers to a mass spectrometer which uses laser as means to desorb, volatilize, and ionize an analyte.

"Detect" as used herein has its ordinary meaning as known to those skilled in the art and refers to identifying the presence, absence or amount of the object to be detected.

The terms "polypeptide," "peptide" and "protein" as used herein have their ordinary meaning as known to those skilled in the art and refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" as used herein has its ordinary meaning as known to those skilled in the art and refers to a composition detectable by spectroscopic, photochemical, biochemical, immunochemical, or chemical means. For example, useful labels include $_{32}P$, $_{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" as used herein has its ordinary meaning as known to those skilled in the art and refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon, and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Immunoassay" as used herein has its ordinary meaning as known to those skilled in the art and refers to an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, as used herein has its ordinary meaning as known to those skilled in the art and refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Energy absorbing molecule" or "EAM" as used herein has its ordinary meaning as known to those skilled in the art and refers to a molecule that absorbs energy from an ionization source in a mass spectrometer thereby aiding desorption of analyte, such as a marker, from a probe surface. Depending on the size and nature of the analyte, the energy absorbing molecule can be optionally used. Energy absorbing molecules used in MALDI are frequently referred to as "matrix." Cinnamic acid derivatives, sinapinic acid ("SPA"), cyano hydroxy cinnamic acid ("CHCA") and dihydroxybenzoic acid are frequently used as energy absorbing molecules in laser desorption of bioorganic molecules.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue and the like. A biological sample can be obtained from a subject by conventional techniques. Blood can be obtained by venipuncture, while plasma and serum can be obtained by fractionating whole blood according to known methods. Surgical techniques for obtaining solid tissue samples are well known in the art.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" as used herein has its ordinary meaning as known to those skilled in the art and refers to any rigid or semi-rigid support to which proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

Any animal that is susceptible to *Helicobacter pylori* infection can be used as a subject from which a biological sample is obtained. For example, the subject can be a mammal, such as for example, a human, dog, cat, horse, cow, pig, sheep, goat, chicken, primate, rat, or mouse. More preferably, the subject is a human. Particularly preferred are subjects suspected of having or at risk for developing *Helicobacter pylori* infection and related *Helicobacter pylori* infection conditions.

The biomarkers herein can be detected in a sample by any means. For example, immunoassays, include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4 degrees C., adding protein A and/or protein G sepharose beads to the cell lysate, incubating for about an hour or more at 4 degrees C., washing the beads in lysis buffer and resuspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell, lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., .sup.32P or .sup.125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen (i.e. *Helicobacter pylori* infection biomarker α-L-fucosidase 2 marker), coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Some aspects of the invention provides a method (also referred to herein as a "screening assay") for identifying modulators, i.e., candidate or test compounds or agents (e.g., peptides, peptidomimetics, small molecules or other drugs) which bind to the polypeptides.

The test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed., Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

Some embodiments of the present invention also pertain to the field of predictive medicine in which diagnostic assays and monitoring clinical trials are used for prognostic (predictive) purposes to thereby treat a subject prophylactically. Accordingly, one aspect of the present invention relates to diagnostic assays for determining a polypeptide marker in the context of a biological sample (e.g., blood, serum, cells, tissue) to thereby determine whether an individual is infected.

An exemplary method for detecting the presence or absence of polypeptide in a biological sample involves obtaining a biological sample from a test subject and contacting the biological sample with a compound or an agent capable of detecting. An exemplary agent for detecting a polypeptide is an antibody capable of binding to the polypeptide, such as an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody. The term "biological sample" is intended to include tissues, cells and biological fluids isolated from a subject, as well as tissues, cells and fluids present within a subject. That is, the detection method of the invention can be used to detect polypeptide in a biological sample in vitro as well as in vivo. For example, in vitro techniques for detection of polypeptide include enzyme linked immunosorbent assays (ELISAs), Western blots, immunoprecipitations and immunofluorescence. Furthermore, in vivo techniques for detection of polypeptide include introducing into a subject a labeled anti-polypeptide antibody. For example, the antibody can be labeled with a radioactive marker whose presence and location in a subject can be detected by standard imaging techniques.

In some embodiments, the biological sample contains polypeptide markers from the test subject.

Some embodiments of the invention also encompass kits for detecting the presence of the polypeptide in a biological sample. For example, the kit can comprise a labeled compound or agent capable of detecting the polypeptide in a biological sample; means for determining the amount of polypeptide in the sample; and means for comparing the amount of polypeptide in the sample with a standard. The compound or agent can be packaged in a suitable container. The kit can further comprise instructions for using the kit to detect polypeptide.

Monitoring the influence of agents (e.g., drugs) on the activity of the polypeptide can be applied not only in basic drug screening, but also in clinical trials. For example, the effectiveness of an agent determined by a screening assay to decrease polypeptide levels can be monitored in clinical trials of subjects exhibiting increased polypeptide levels.

In some embodiments, the present invention provides a method for monitoring the effectiveness of treatment of a subject with an agent (e.g., a small molecule, or other drug candidate identified by a screening assay) including the steps of (i) obtaining a preadministration sample from a subject prior to administration of the agent; (ii) detecting the level of polypeptide in the preadministration sample; (iii) obtaining one or more post-administration samples from the subject; (iv) detecting the level of polypeptide in the post-administration samples; (v) comparing the level of polypeptide in the pre-administration sample with the polypeptide in the post administration sample or samples; and (vi) altering the administration of the agent to the subject accordingly.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

EXAMPLES

The following examples are included merely for purposes of illustration of certain aspects and embodiments of the present invention, and are not intended to limit the invention.

Example 1

Figure 2A:
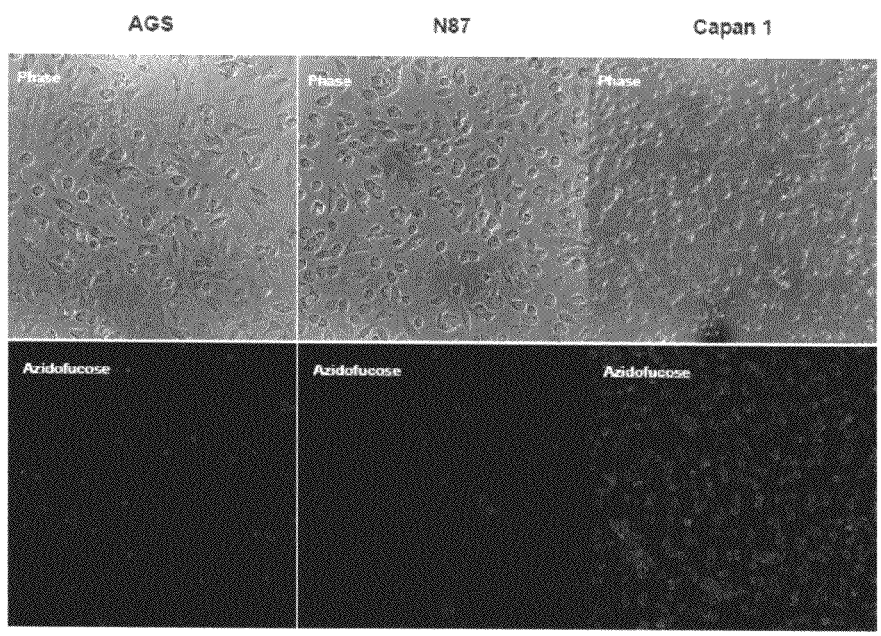
FIG. 2A is a fluorescent imaging of fucosylation by incubating AGS, N87 and Capan 1 cells with tetra-O-acetyl-6-azido-L-fucose and then subsequently staining these cells with 1,8-naphthalimide alkyne. Click chemistry was applied by reaction of the azide group with 1,8-naphthalimide alkyne to yield fluorogenic fucosylated glycans (green).

H. pylori Extracts 6-Azido-L-Fucose from Human Epithelial Fucosylated Glycoconjugates A considerable proportion of H. pylori in the stomach is located at the epithelial mucosa (Schreiber S, et al. Proc. Natl. Acad. Sci. USA 2004, 101:5024-5029) where there are various fucose-containing oligosaccharides including Lewis antigens. To determine if H. pylori acquires L-fucose from host cells, similar to the interaction between B. thetaiotaomicron and small intestine cells (Hooper, et al. Proc. Natl. Acad. Sci. USA 1999, 96:9833-9838), the click chemistry-based fluorogenic labeling method developed by Wong and coworkers (Sawa M, et al. Proc. Natl. Acad. Sci. USA 2006, 103:12371-12376) was applied to detect fucosylated glycoconjugates. Fucosylated glycoconjugates in cultured whole cells were labeled with tetra-O-acetyl-6-azido-L-fucose. The acetyl groups improve cell permeability of the sugar probe, and they are later removed by non-specific esterases (to yield 6-azido-L-fucose) inside cells before the sugar is incorporated into the biosynthetic pathway (FIG. 1). Human gastric adenocarcinoma epithelial cells (AGS and N87) and pancreatic adenocarcinoma cells (Capan 1, expressing gastric-type mucins) were incubated with tetra-O-acetyl-6-azido-L-fucose for 72 h, intensively washed to remove the unincorporated sugar, and then coupled with a 1,8-naphthalimide alkyne probe by click chemistry for fluorogenic detection. Fluorescence microscopy images indicated that AGS, N87 and Capan 1 cells incorporated the modified L-fucose residue and transformed it into fucosylated glycoconjugates on the cell surface (FIG. 2A). Capan 1 and AGS cells were chosen for further analysis due to their relatively high rate of L-fucose incorporation.

Figure 2B:
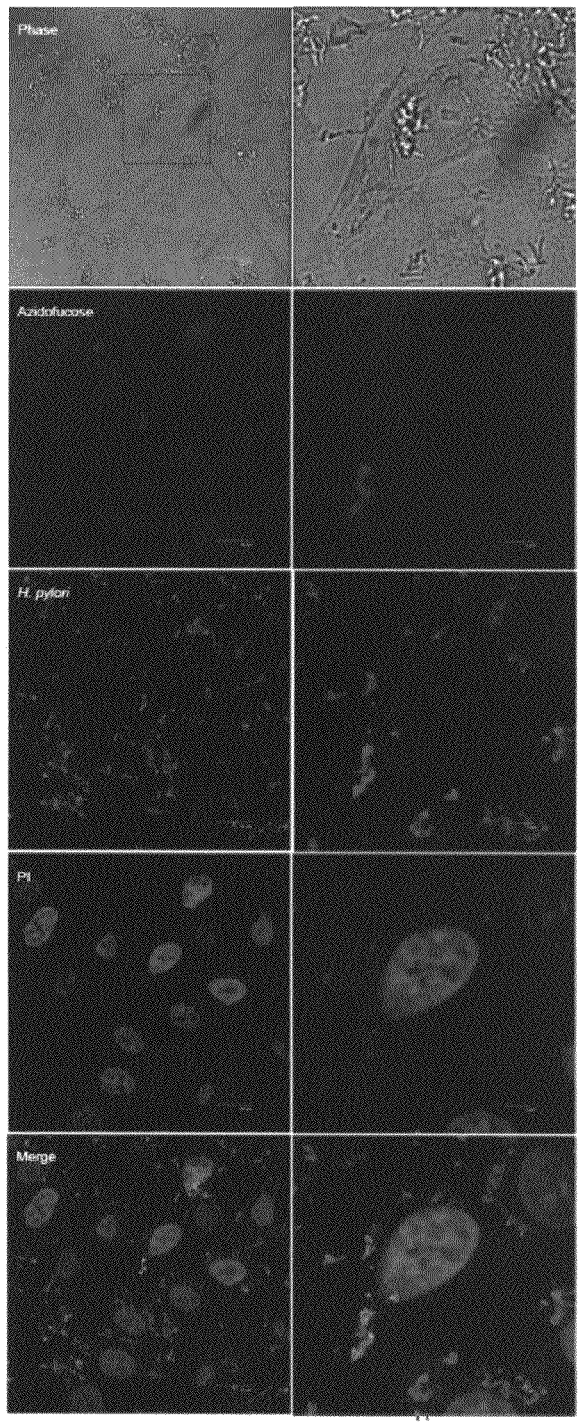
FIG. 2B is a fluorescent imaging of Capan 1 cells incubated with 200 μM tetra-O-acetyl-6-azido-L-fucose for 72 h, intensively washed five times with PBS, and then infected with *H. pylori* for 4 h. Cells were fixed, labeled with 1,8-naphthalimide alkyne (blue), stained with *H. pylori*-specific antibody (Alexa Fluor 488, green) and the nuclei-specific dye propidium iodide (PI, red), and examined by confocal fluorescence microscopy. Overlay appears as light green. Upper panel scale bar, 20 μm. Lower panel scale bar, 5 μM.
Figure 3:
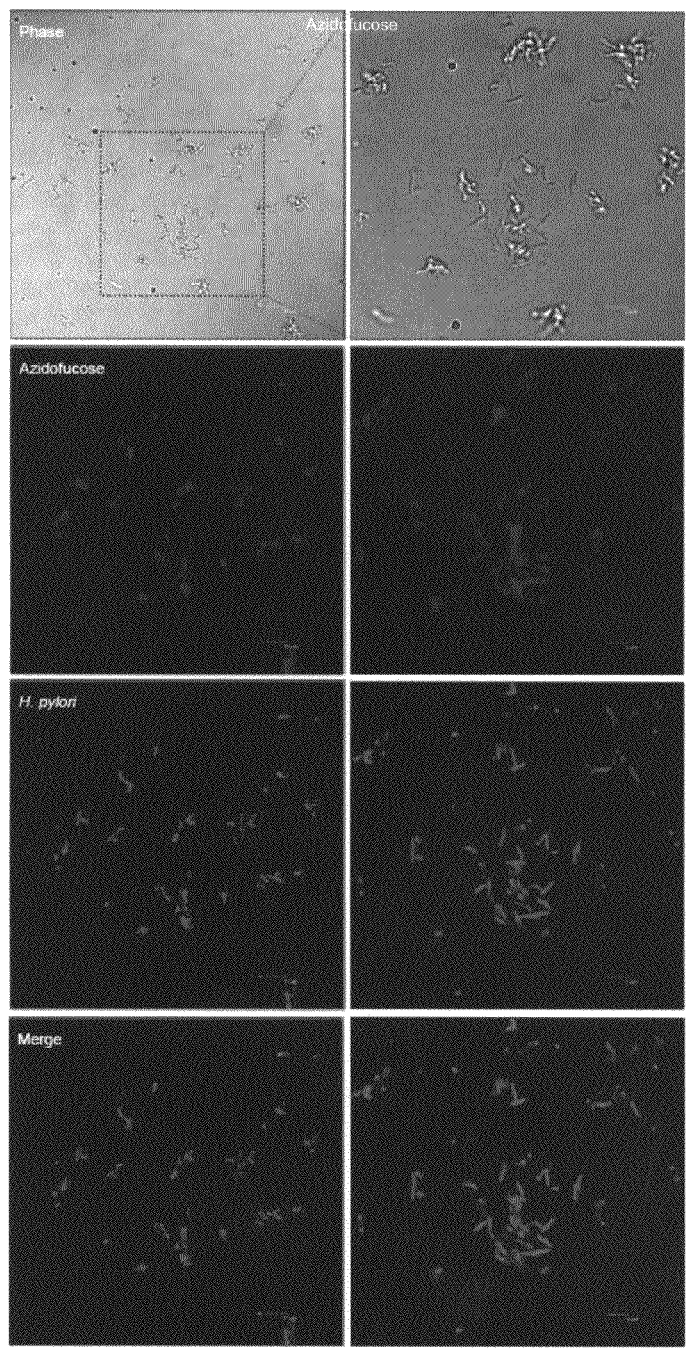
FIG. 3 is a fluorescent imaging of *H. pylori* taking up 6-azido-L-fucose directly from the host culture medium. *H. pylori* was incubated with 200 μM 6-azido-L-fucose for 4-8 h, washed extensively five times with PBS. The bacteria was fixed, labeled with a click-activated fluorescent probe (blue), stained with *H. pylori*-specific antibody (conjugated to Alexa Fluor 488, green), and examined by confocal microscopy. Co-localization is shown as light blue. Left panel scale bar, 10 μm. Right panel scale bar, 5 μm.

Capan 1 (labeled with blue fluorescent azidofucose) and H. pylori (green labeled with Alexa Fluor 488) cells were found to be co-localized at the epithelial surface (FIG. 2B), which increased in a time-dependent manner, indicating that adherent H. pylori takes up 6-azido-L-fucose (FIG. 2B (4 h) and FIG. 3 (8 h)). Furthermore, H. pylori could also directly take up 6-azido-L-fucose (FIG. 3). Thus, H. pylori potentially obtains L-fucose directly from the plasma membrane of host cells.

Example 2

Figure 4A:
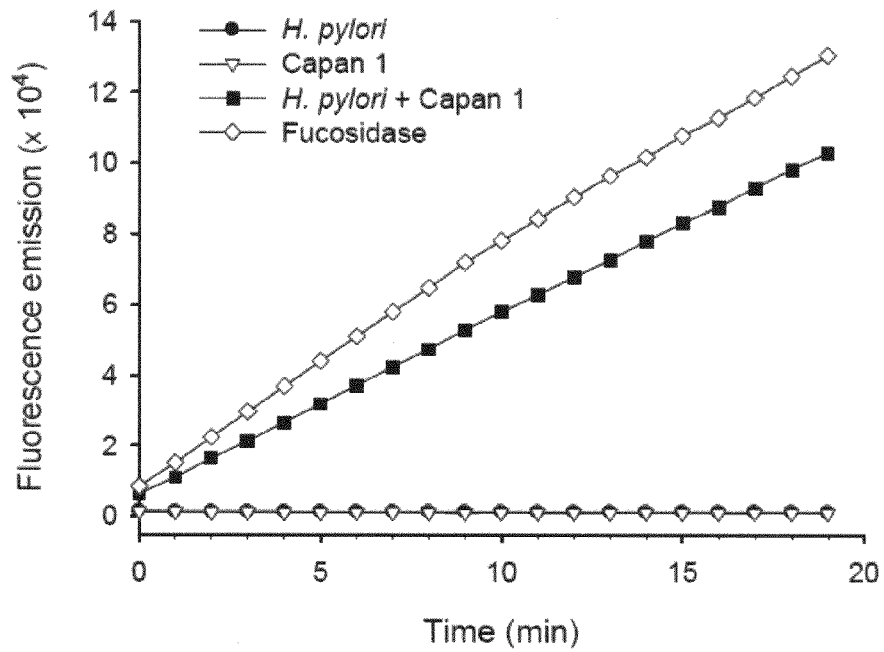
FIGS. 4A-4C illustrate activity assay, purification and identification of the secreted α-L-fucosidase from host cells co-cultured with *H. pylori*. Capan 1 (4A) and five gastric adenocarcinoma cell lines (4B, 4C) were examined, including AGS, AZ-521, KATO III, N87 and TSGH 9201. Before enzymatic activity measurement, cell culture media were subjected to affinity chromatography using a column packed with FNJ-immobilized Sepharose beads.
Figure 4B:
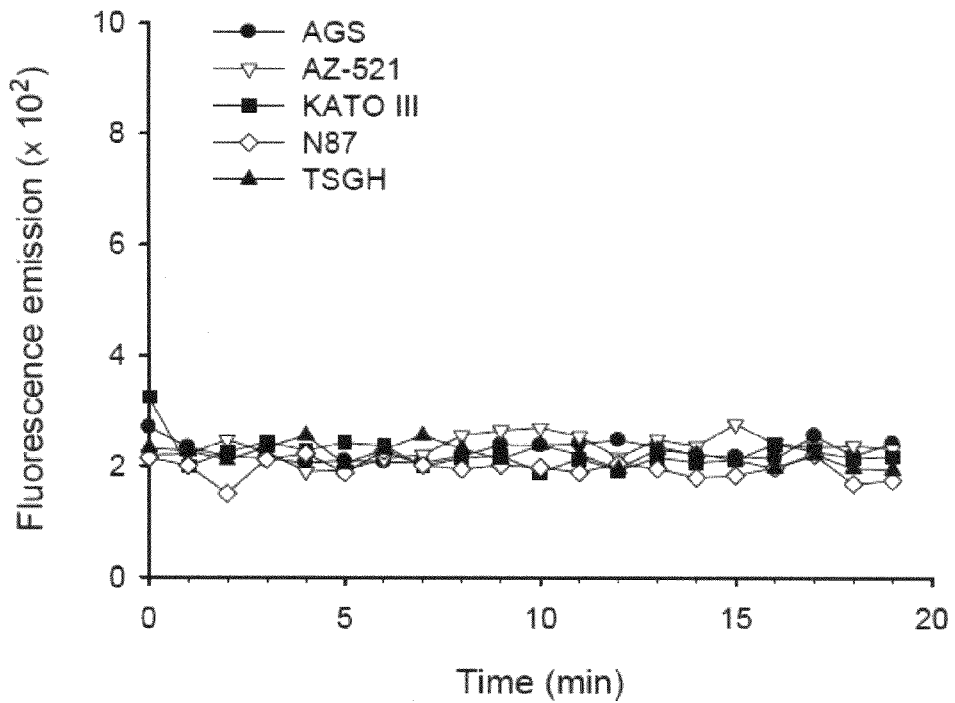
Figure 4C:
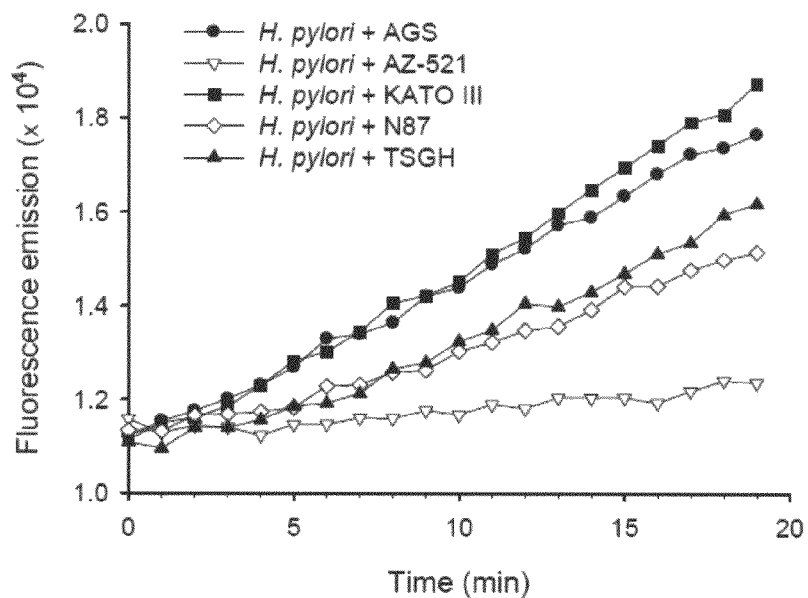
Figure 4D:
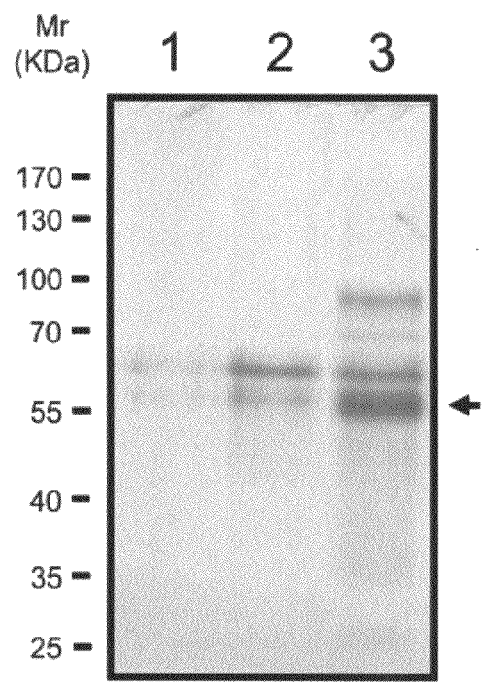
FIG. 4D provides analysis of the enzymatically active pooled fractions obtained from the affinity chromatography-based purification by SDS-PAGE. The gel was stained with silver nitrate. Lane 1, *H. pylori* culture supernatant (~2×10$^{10}$ cells) was used for the purification. Lane 2, Capan 1 cell culture supernatant (~1×10$^8$ cells). Lane 3, Co-culture supernatant of Capan 1 and *H. pylori* (MOI, 1:200). The predominant ~55-kDa band, indicated by an arrow, was clearly visualized in Lane 3 as compared with Lanes 1 and 2.
Figure 4E:
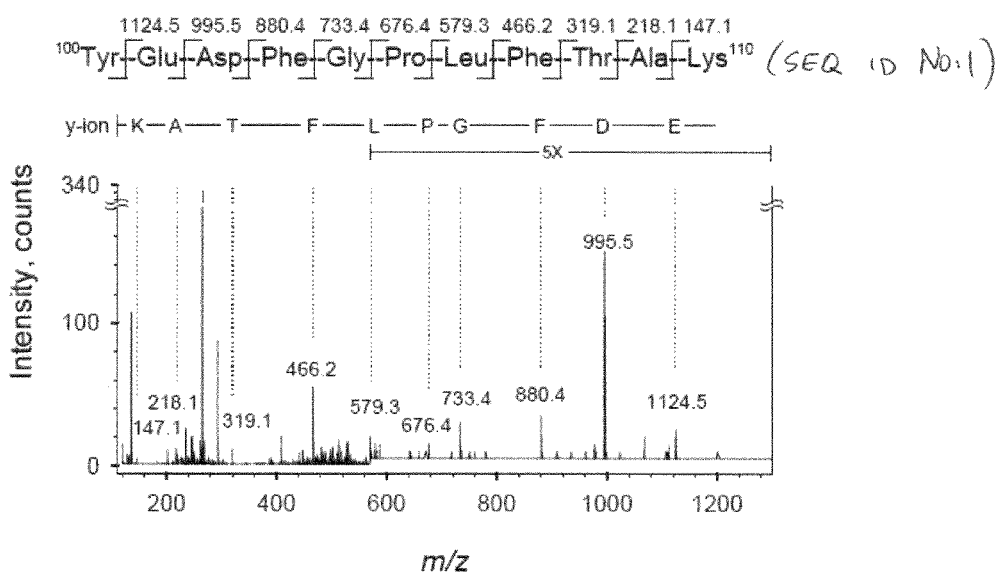
FIG. 4E shows identification of α-L-fucosidase 2 (FUCA2) by mass spectrometer. MS/MS spectrum of the signal [M+2H]$^{2+}$ at m/z 644.3 corresponded to the sequence $^{100}$YEDFGPLFTAK$^{110}$ of FUCA2 (the second shaded sequence in FIG. 5). Only the most intense y-series fragment ions were labeled with single letter codes.

Detection of α-L-Fucosidase Activity from Host Cells in Response to H. pylori Infection Transfer of L-fucose from host cells to H. pylori requires the presence of an α-L-fucosidase to specifically remove L-fucose from fucosylated glycans. To detect α-L-fucosidase activity, co-culture supernatants were concentrated approximately 10-fold and then subjected to an affinity chromatography column packed with α-L-fucosidase inhibitor-immobilized agarose beads [the inhibitor was 1-aminomethyl-1-deoxy-fuconojirimycin (FNJ)]. 4-Methylumbelliferyl-α-L-fucoside (4MU-fucoside) was utilized as the substrate to measure α-L-fucosidase activity in the resulting fractions. Substantial enzyme activity (309 U/108 host cells; 1 U is defined as hydrolysis of 1 μmol of 4MU-fucoside per min at pH 5.5, 25° C.) was detected from the co-culture medium 4 h after inoculation at the ideal multiplicity of infection (MOI of ~200:1). In contrast, no enzyme activity was detected in either uninfected Capan 1 cells or H. pylori alone (FIG. 4A). Similar results were observed in studies of other human gastric adenocarcinoma cell lines including AGS, AZ-521, KATO III, N87 and TSGH 9201 (FIGS. 4B and 4C). The fractions containing enzyme activity were pooled and then examined by SDS-PAGE. Only two major bands were visible in the pooled fraction as compared with individual culture samples from Capan 1 or H. pylori cells. The predominant ~55-kDa band (FIG. 4D, arrow) was identified as FUCA2 by in-gel tryptic digestion and LC-MS/MS (FIG. 4E). It was proposed that FUCA2 is a secreted hydrolase (residing at chromosome locus 6q24) that is genetically distinct from lysosomal α-L-fucosidase 1 (FUCA1, residing at chromosome locus 1p34). See Intra, et al., Gene 2007, 392:34-46. Although the two α-L-fucosidases are very similar at the amino acid sequence level (55% identity and 69% similarity), two unique peptides of FUCA2 were identified by the LC-MS/MS analysis (FIG. 5). For instance, the fragment ion in the MS/MS spectrum of a doubly charged ion m/z 624.3 corresponded to the peptide sequence, 100YEDFG-FLFTAK110 (FIG. 4E), which is unique to FUCA2. It is noted that the secretion of FUCA2 was not a consequence of cell death because cell viability was not affected by H. pylori infection. Additionally, human FUCA1 and FUCA2 were prepared and characterized. The result indicated that the modification at C6-position of L-fucose is acceptable to both enzymes and does not affect the kinetic parameters, in comparison with L-fucose-containing substrate or inhibitor.

Example 3

Correlation of Secreted α-L-Fucosidase with H. pylori Adhesion

Figure 6:
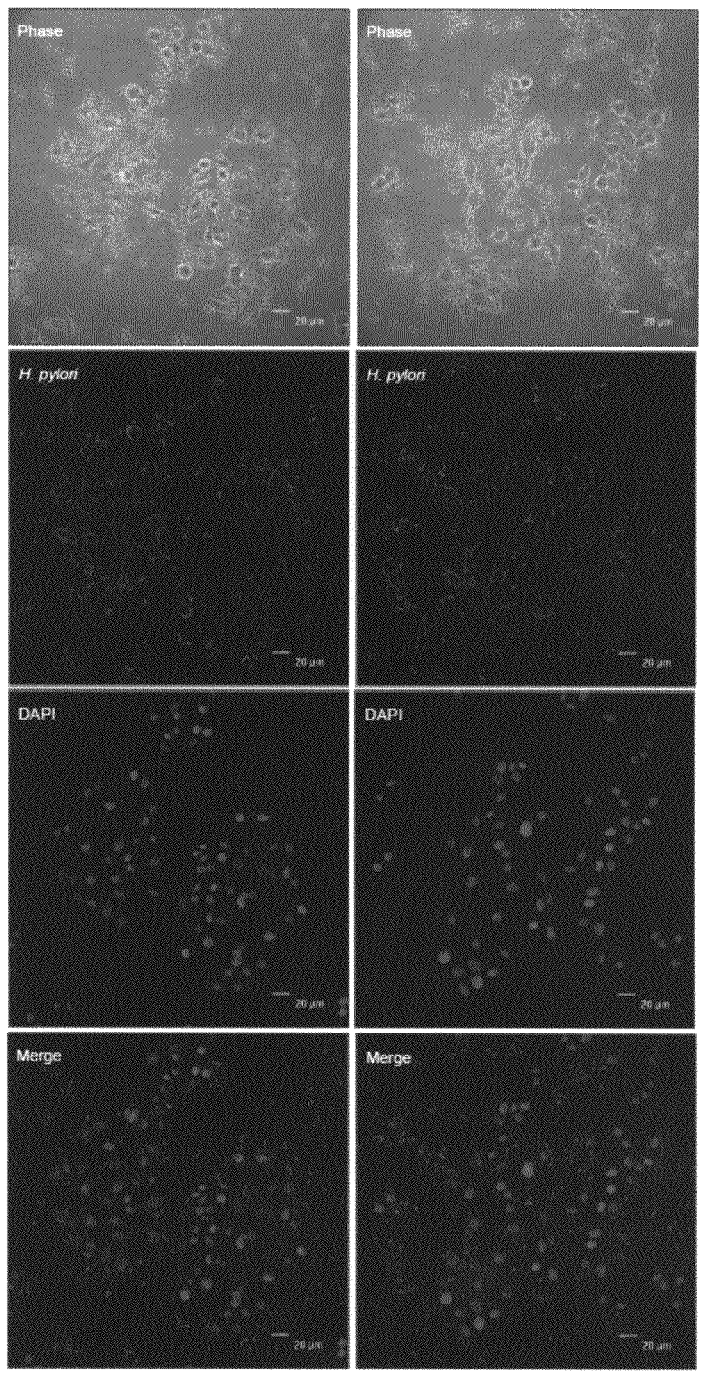
FIG. 6 shows that secreted FUCA2 is associated with *H. pylori* adhesion to host cells. Both mock-transfected Capan 1 cells and stable FUCA2-knockdown Capan 1 cells (Capan 1-FUCA2 K.D.) were incubated with *H. pylori* for 4 h and then doubly stained with anti-*H. pylori* (conjugated to Alexa Fluor 488, green) and a nuclei-specific dye (DAPI, red). Mock-transfected Capan 1 and Capan 1-FUCA2 K.D. cells were both infected by a comparable number of H. pylori. After 4 h, the number of adherent H. pylori was almost identical in both cell lines, which differs from the number of adherent H. pylori after 8 h (see FIG. 7A).
Figure 7A:
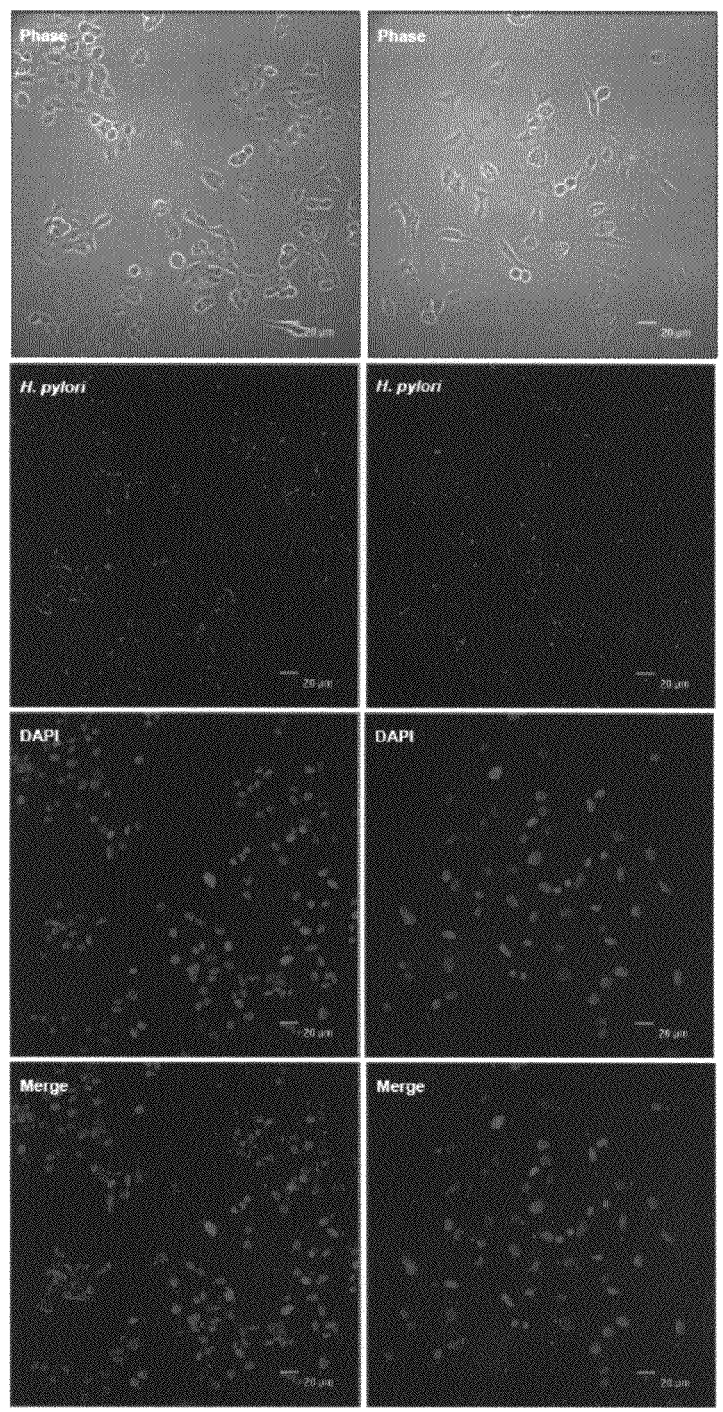
FIG. 7A-7C collectively illustrate that FUCA2 is associated with for H. pylori adhesion to host cells.

B. thetaiotaomicron produces a fucose-sensing protein that induces the host intestine to increase the expression of fucosylated glycans and secretes bacterial α-L-fucosidase to harvest L-fucose for import and metabolic processing (Hooper, et al., Proc. Natl. Acad. Sci. USA 1999, 96:9833-9838). In contrast, FUCA2 is secreted by the host in response to H. pylori infection, releasing L-fucose residues from the host cell surface. Because fucosylated blood group antigens are important for host-microbe interactions, the potential correlation between FUCA2 and H. pylori adhesion was investigated. The attachment of H. pylori was examined using confocal fluorescence microscopy by co-culturing H. pylori in mock-transfected Capan 1 cells or stable FUCA2-knockdown Capan 1 cells (Capan 1-FUCA2 K.D.). With a short-term incubation (4 h), the pathogen attached equally well to both mock-transfected and stable FUCA2-knockdown Capan 1 cells (FIG. 6). With prolonged incubation (8 h), however, H. pylori attachment to Capan 1-FUCA2 K.D. cells decreased by ~50% as compared with mock-transfected cells (FIG. 7A). The number of viable Capan 1 cells did not differ significantly between co-cultures containing mock-transfected or stable FUCA2-knockdown Capan 1 (data not shown).

The results clearly show correlation between secreted α-L-fucosidase and H. pylori adhesion to the host cells.

Example 4

Measurement of the Adhesion Efficiency of H. pylori

Figure 7B:
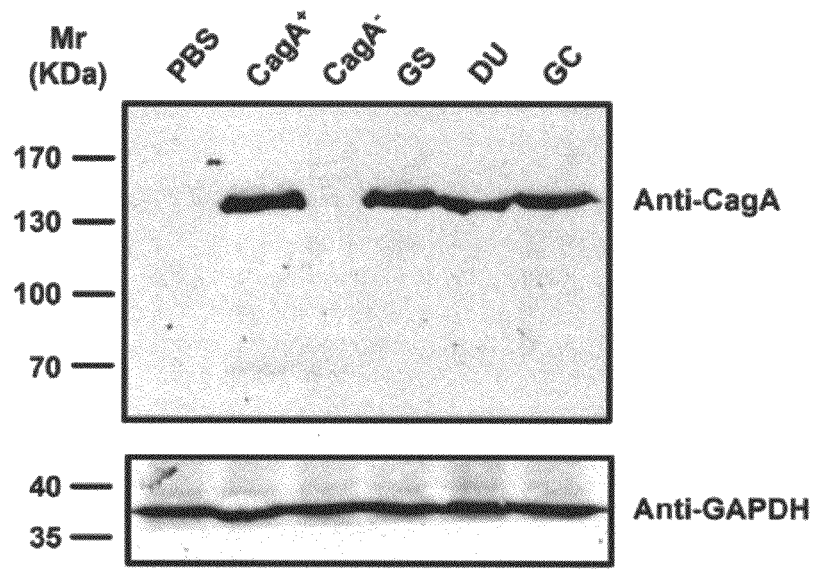
Figure 7C:
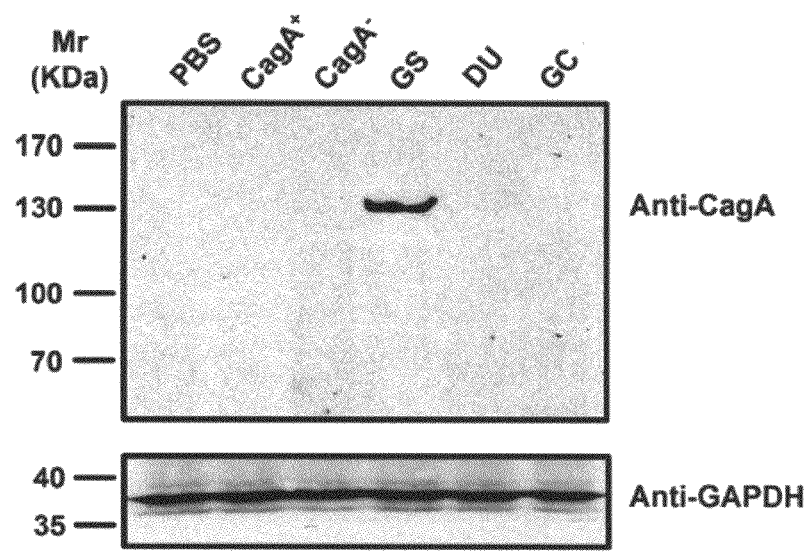
Figure 8A:
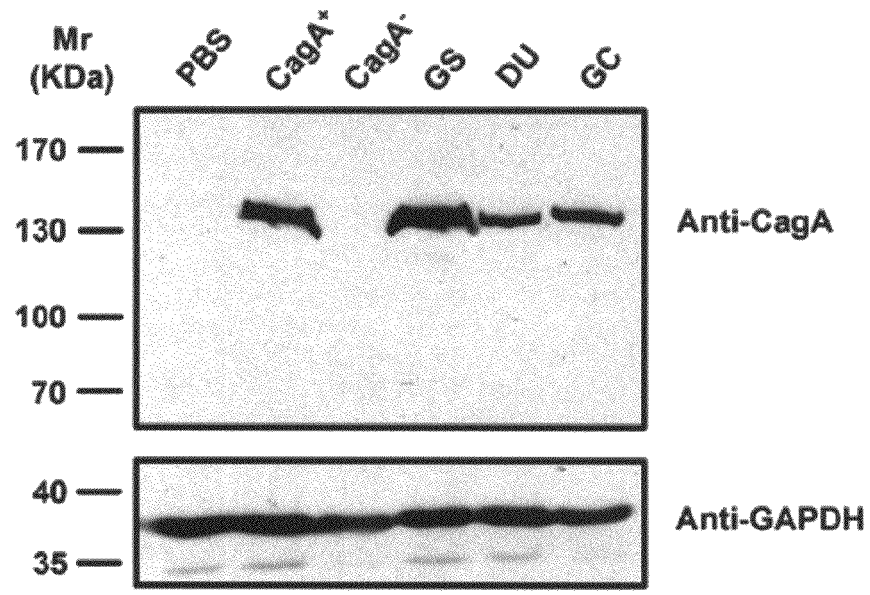
FIG. 8A-8D collectively provide immunoblot analysis of epithelial cells infected with H. pylori using mouse monoclonal anti-CagA. Capan 1 and AGS cells were infected with different H. pylori strains, including CagA$^+$ and CagA$^-$, and various clinical isolates from patients with gastritis (GS), duodenal ulcer (DU) and gastric cancer (GC). PBS represents the negative control. The co-culture was maintained for 6-8 h at an MOI of ~200:1. In the parallel experiments, Capan 1 (a) and AGS cells (c) were infected under the same conditions. The effect of α-L-fucosidase was evaluated by addition of 100 μM FNJ to the co-cultures of Capan 1 (b) and AGS cells (d) with various H. pylori strains.
Figure 8B:
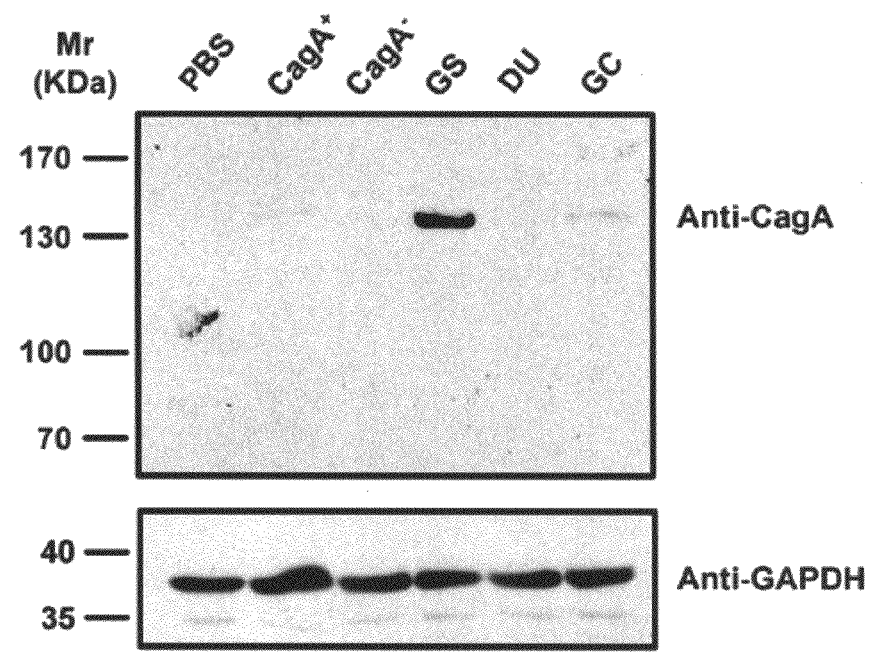
Figure 8C:
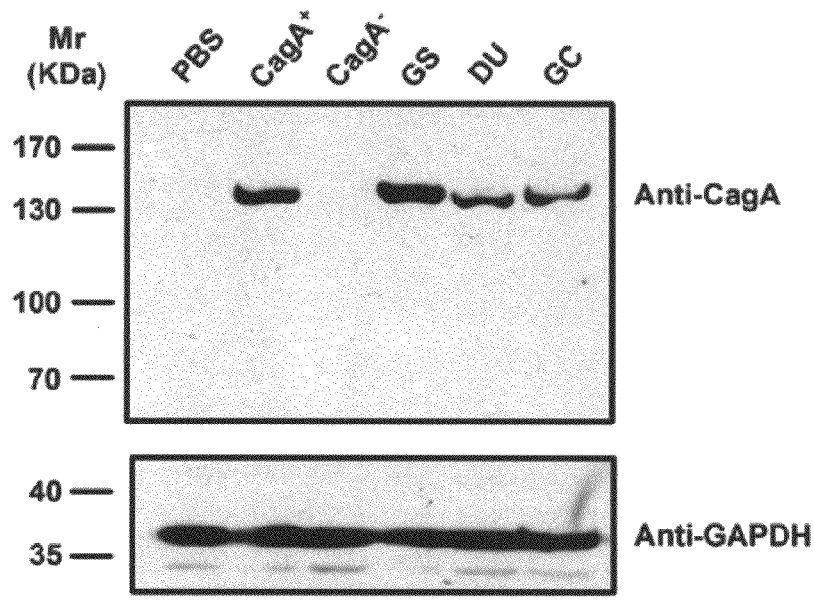
Figure 8D:
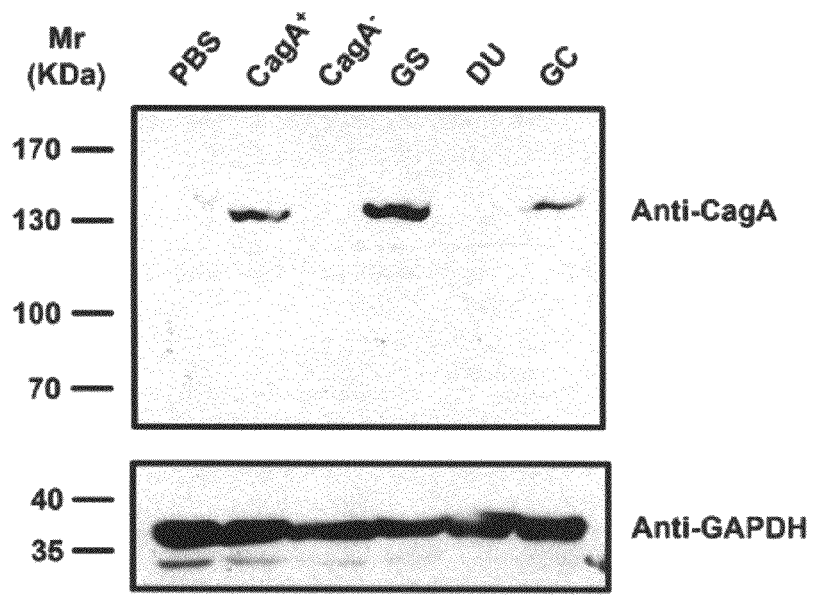

CagA of H. pylori was the first reported bacterial virulence protein translocated by a type IV secretion system (Stein, et al., Proc. Natl. Acad. Sci. USA 2000, 97:1263-1268). Translocated CagA protein can be detected inside host cells soon after H. pylori attachment. The adhesion efficiency of H. pylori can be thus measured by monitoring the level of translocated CagA inside host cells. Four different epithelial cell lines were chosen for the study, namely mock-transfected Capan 1, Capan 1-FUCA2 K.D., Capan 1, and AGS cells. Isogenic vacA (CagA+), cagA (CagA−) mutants, and clinical isolates from patients with gastritis (GS), duodenal ulcer (DU), and gastric cancer (GC) were selected for co-culturing with the four epithelial cell lines. The epithelial cell lysates were analyzed by SDS-PAGE 6-8 h after infection and immunoblotted with a CagA-specific monoclonal antibody. CagA (~140 kDa) was detected when mock-transfected Capan 1 cells were infected with each different *H. pylori* strain (FIG. 7B). Nonetheless, CagA was not detected upon Capan 1-FUCA2 K.D. infection with the different *H. pylori* strains, with the exception of GS (FIG. 7C). Likewise, Capan 1 and AGS cells were treated with 100 μM FNJ (an α-L-fucosidase inhibitor), followed by infection with each *H. pylori* strain for 6-8 h. The treatment of Capan 1 or AGS cells with FNJ was found to considerably reduce the transfer of 6-azido-L-fucose from host cells to *H. pylori* (FIG. 7A). Flow cytometric analysis also demonstrated a similar result (FIGS. 7B, 7C). As shown in FIG. 8B, no or little CagA was detected when Capan 1 was treated with FNJ and infected with DU- or GC-specific *H. pylori* strains. These results are also consistent with those obtained in AGS cells (FIG. 8D). In contrast, CagA was detected in substantial amounts without FNJ treatment (FIGS. 8A and 8C, corresponding to the results of Capan 1 and AGS cells, respectively). Notably, the level of CagA was not affected by FNJ in the co-culture infected with the GS-specific strain, indicating that α-L-fucosidae activity is associated with *H. pylori* attachment, especially for strains isolated from patients with DU or GC.

Figure 9A:
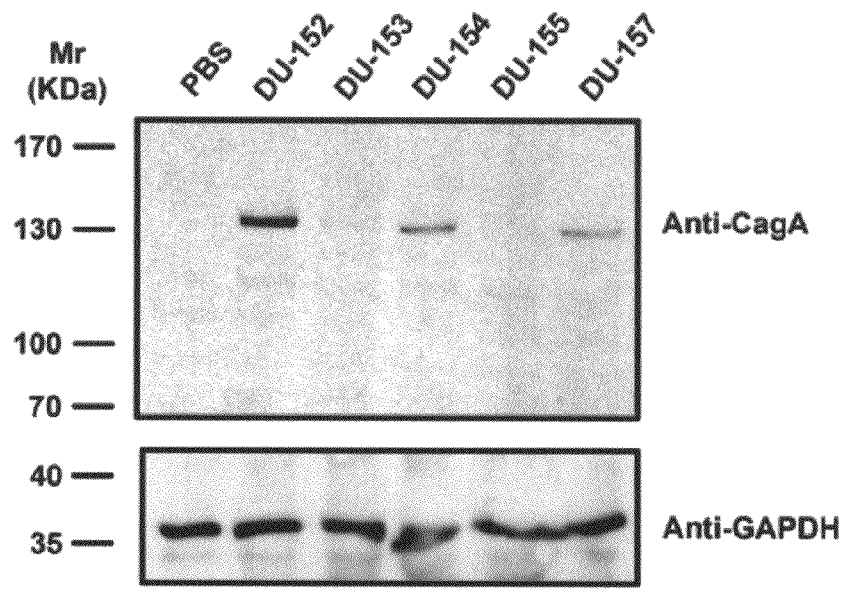
FIG. 9 illustrates immunoblot analysis of H. pylori-infected epithelial cells with mouse monoclonal anti-CagA. Capan 1 and AGS cells were infected with different H. pylori strains that were clinical isolates from five different patients with duodenal ulcer (DU). PBS was used as a negative control in the absence of H. pylori. The co-culture was maintained for 6-8 h at an MOI of ~200:1. In parallel experiments, Capan 1 and AGS cells were infected under the same conditions, respectively (a, c). The effect of α-L-fucosidase was evaluated by addition of 100 μM of the α-L-fucosidase inhibitor, FNJ, to co-cultures of Capan 1 (b) and AGS cells (d) with the indicated H. pylori strains. GAPDH was used as a loading control in all blots.
Figure 9B:
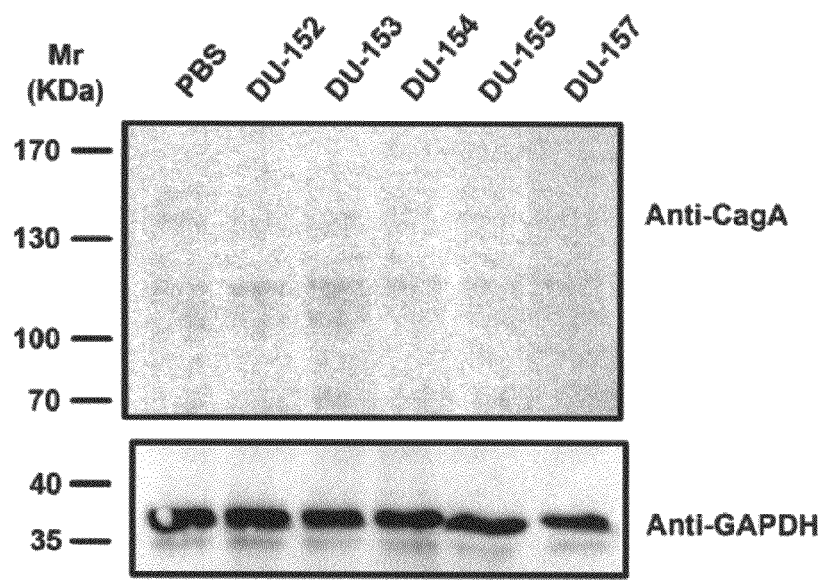
Figure 9C:
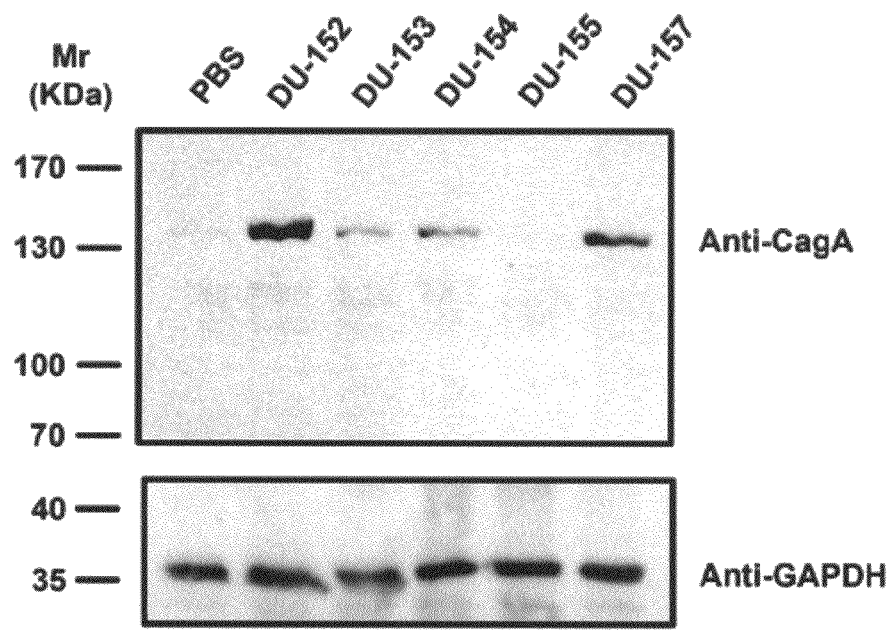
Figure 9D:
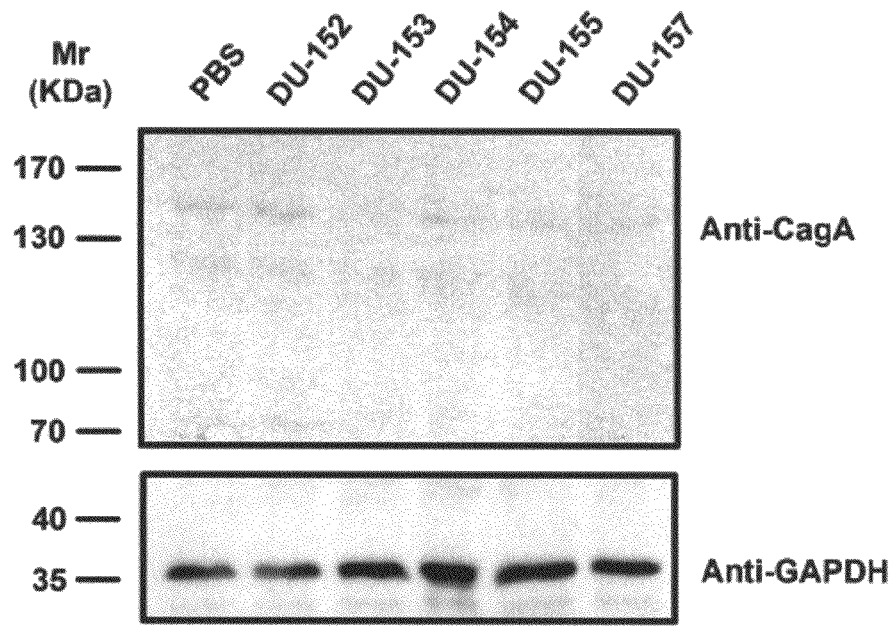

Furthermore, to determine if the observed dependence of *H. pylori* attachment on FUCA2 is related to specific types of gastric disease, a number of DU- and GC-specific strains were clinically isolated and evaluated as described previously. Capan 1 and AGS cells were infected with DU-specific strains of *H. pylori* in the absence (FIGS. 9A and 9C) or presence of 100 μM FNJ (FIGS. 9B and 9D). Five DU strains, DU-152, DU-153, DU-154, DU-155 and DU-157, were further examined. DU-156 was examined previously (FIGS. 7B and 7C and FIG. 8A-8D). Examination of DU-specific strains indicated that CagA was no longer present upon FNJ treatment under co-culture conditions that fostered CagA expression.

Example 5

Investigation of the L-Fucose-Related Biosynthesis Via α-L-Fucosidase Activity

Figure 10A:
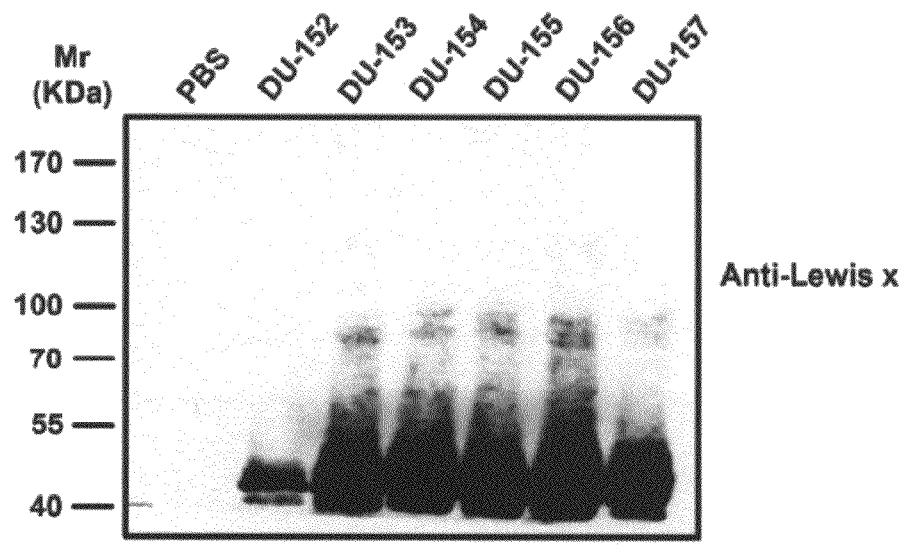
FIG. 10A-10B collectively show immunoblot analysis of H. pylori-infected Capan 1 cells with mouse monoclonal anti-Le$^x$ antigen. Mock-transfected Capan 1 and Capan 1-FUCA2 K.D. cells were infected with different H. pylori strains (from DU-152 to DU-157) that were clinical isolates from six different patients with duodenal ulcer (DU). PBS represents a negative control in the absence of H. pylori. The co-culture was maintained for 12 h at an MOI of ~400:1. In the parallel experiments, mock-transfected Capan 1 (a) and Capan 1-FUCA2 K.D. cells (b) were infected under the same conditions. The bacterial cells were collected and lysed for the Le$^x$ analysis. Le$^x$-containing glycoproteins were found to greatly increase in the H. pylori cells co-cultured with mock-transfected Capan 1 cells (a), in contrast to those in the H. pylori cells co-cultured with Capan 1-FUCA2 K.D. cells (b).
Figure 10B:
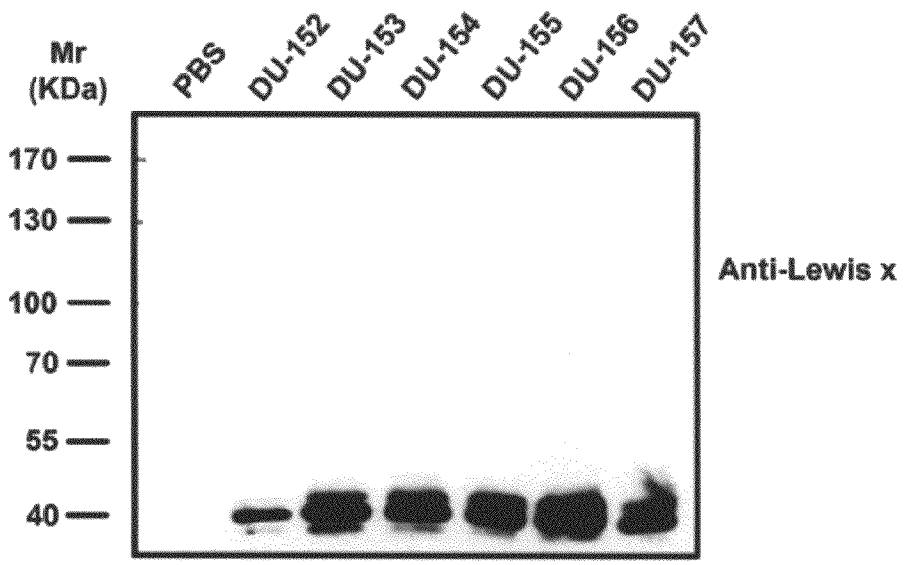
Figure 11A:
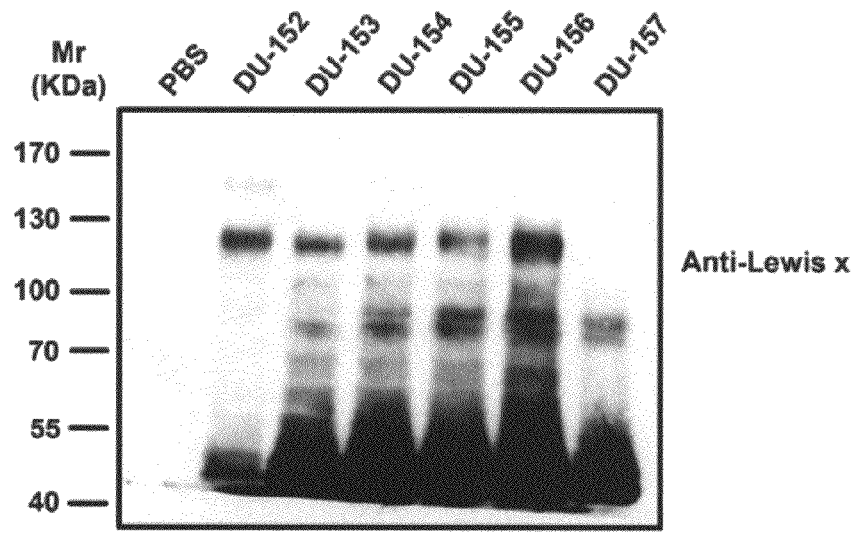
FIGS. 11A-11D collectively show immunoblot analysis of H. pylori-infected Capan 1 and AGS cells with mouse monoclonal anti-Le$^x$ antigen. Capan 1 and AGS cells were infected with different H. pylori strains (from DU-152 to DU-157) that were clinical isolates from six different patients with duodenal ulcer (DU). PBS represents a negative control in the absence of H. pylori. The co-culture was maintained for 12 h at an MOI of ~400:1. In the parallel experiments, Capan 1 (11a) and AGS cells (11c) were infected under the same conditions. The effect of α-L-fucosidase was evaluated by addition of 100 μM FNJ to the co-cultures of Capan 1 (11b) and AGS cells (11d) with various H. pylori strains. The bacterial cells were collected and lysed for Le$^x$ analysis. Le$^x$-containing glycoproteins were found to be significantly less in Capan 1 and AGS cells in the presence of FNJ.
Figure 11B:
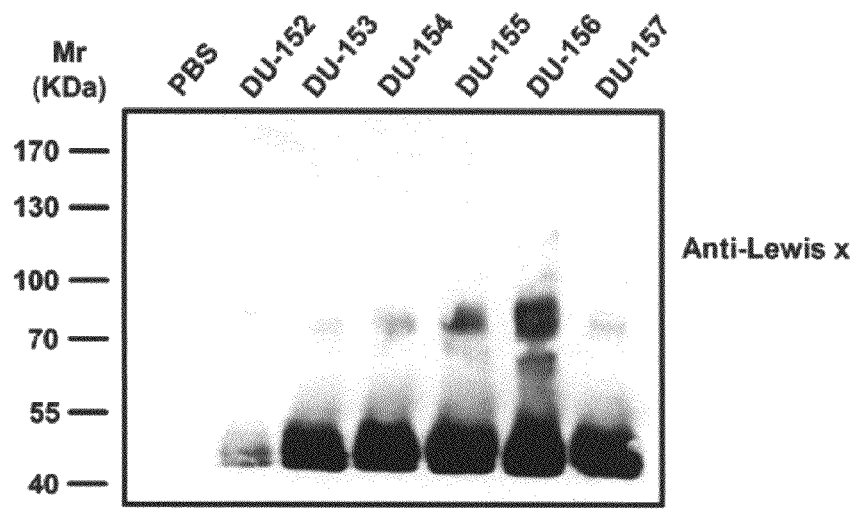
Figure 11C:
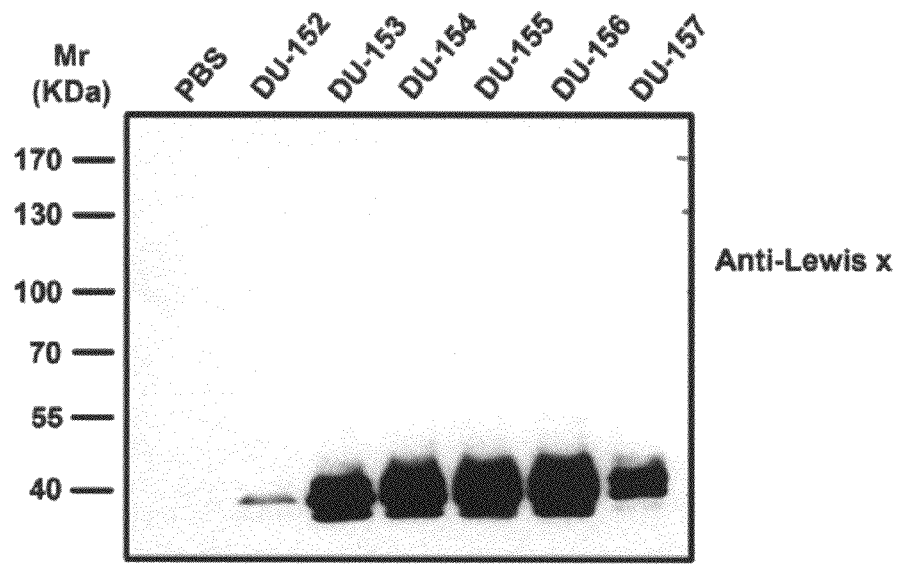
Figure 11D:
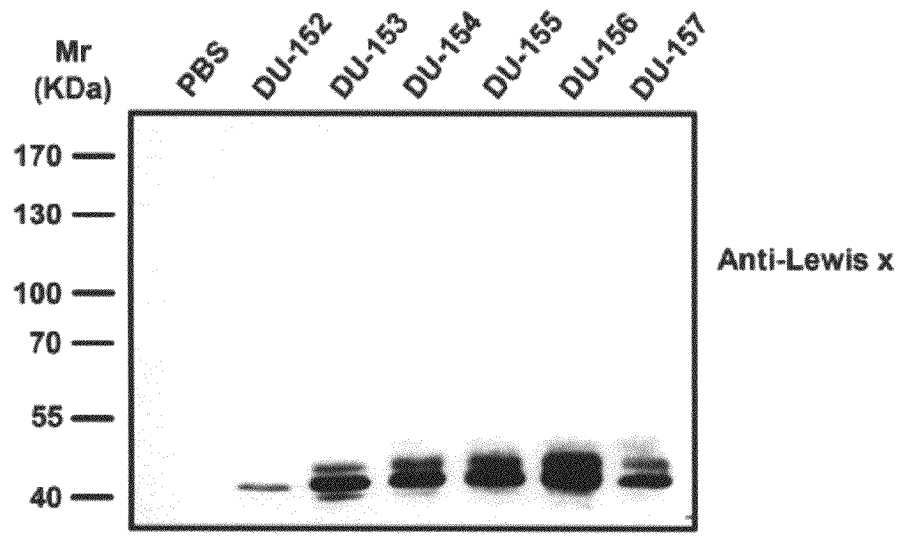

The secretion of FUCA2 directly results in the extracellular production of L-fucose residues that are then incorporated into *H. pylori*. It is important to determine if the L-fucose-related biosynthesis is affected at the same time. Mock-transfected Capan 1 and Capan 1-FUCA2 K.D. were both infected with six *H. pylori* DU-specific strains (from DU-152 to DU-157). The *H. pylori* cell lysates were analyzed by SDS-PAGE 12 h after infection and immunoblotted with a Le$^x$-specific monoclonal antibody. An elevated level of Le$^x$-containing glycoproteins was observed in *H. pylori* when mock-transfected Capan 1 cells were infected (FIG. 10A), as compared to the limited Le$^x$-expression in the *H. pylori* cells that were co-cultured with Capan 1-FUCA2 K.D. cells (FIG. 10B). Meanwhile, Capan 1 and AGS cells were treated with 100 μM FNJ, followed by infection with the same *H. pylori* DU-specific strains for 12 h. The treatment of Capan 1 or AGS cells with FNJ was found to considerably reduce the Le$^x$-expression level in *H. pylori* (FIGS. 11B and 11D). In contrast, Le$^x$-containing glycoproteins were detected in substantial amounts without FNJ treatment (FIGS. 11A and 11C, corresponding to *H. pylori*-infected Capan 1 and AGS cells, respectively). These results indicate that α-L-fucosidase activity is associated with the level of Le$^x$ antigen in *H. pylori*.

Figure 12:
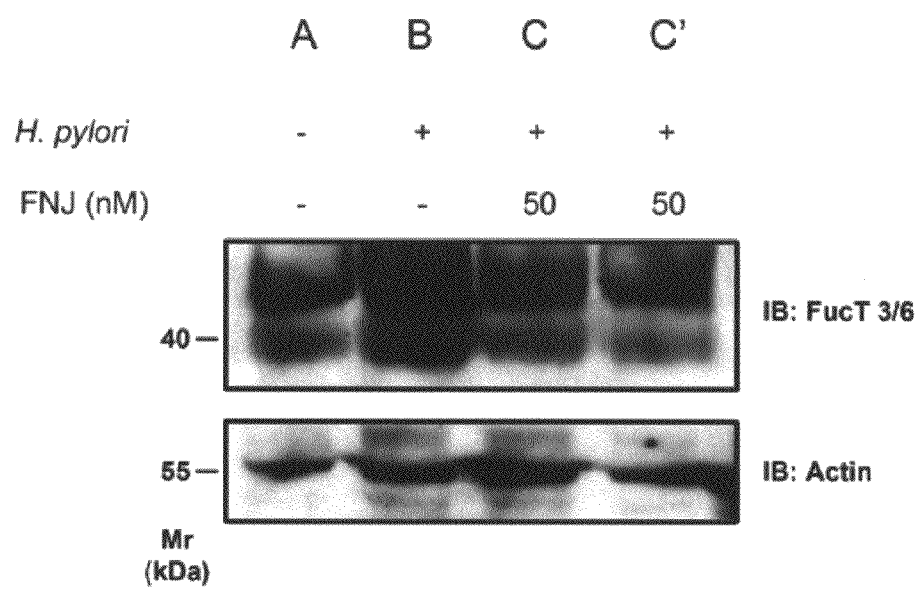
FIG. 12 shows immunoblot analysis of Capan 1 cells infected with H. pylori and blotted with anti-Fut 3/6. Lane A, extract of Capan 1 cells. Lane B, extract of Capan 1 cells pre-treated with H. pylori for 4 h. Lanes C, C', duplicate independent experiments of extract of Capan 1 cells pre-treated with H. pylori and 50 nM of the α-L-fucosidase inhibitor, FNJ, for 4 h.

L-Fucose is a likely source of utilizable carbon and energy because it is located at the termini of mammalian glycoconjugates. L-Fucose is an abundant component of many host gastric mucosa glycoconjugates (Madrid, et al., J. Histochem. Cytochem 1998, 46:1311-1320) that are constitutively synthesized by host cells. Thus, the "request" from *H. pylori* to manufacture fucosylated glycans may require the host to activate translation of one or more of its fucosyltransferase proteins. The expression of human FUT3 and FUT6 decreased substantially in response to FNJ treatment (FIG. 12), suggesting that levels of L-fucose may be regulated in host cells to avoid wasting energy.

Upon depletion of FUCA2 by RNA interference and detection of translocated CagA (a virulence factor of *H. pylori*) in host cells, FUCA2 was found to be associated with *H. pylori* adhesion, in particular to the gastric cancer- and duodenal ulcer-specific strains. Additionally FUCA2 was shown to significantly enhance the expression of Lewis x antigen in *H. pylori*, which is associated with the bacterial cell adhesion in the pathogenesis and defense strategy to escape from host surveillance.

Example 6

Mass Spectrometry Conditions

Protein identification was performed by LC-MS/MS analysis using a quadrupole/time-of-flight mass spectrometer (Qstar Pulsar). Each tryptic digest was resuspended in 10 μl of 5% acetonitrile/0.1% formic acid and loaded onto an autosampler (HP1200) that was coupled with an HP 1100 series binary pump with on-line flow splitter. All samples were injected into a 2 cm×100 μm trapping column and 12 cm×75 μm separation column packed in-house (magic C18, Michrom BioResource, Auburn, Calif.). HPLC mobile phase consisted of $H_2O$ containing 0.1% (v/v) formic acid and acetonitrile-containing 0.1% (v/v) formic acid. Peptide fragmentation by collision-induced dissociation was performed automatically using an information-dependent acquisition option in Analyst QS v1.1 (Applied Biosystems). MASCOT software (v2.1.0, Matrix Science, London, UK) was used to search the MS/MS data against the International Protein Index Human Database for protein identification. The mass tolerance of both precursor ions and the MS/MS fragment ions was set at ±0.3 Da with variable modification of carbamidomethyl cysteine, methionine oxidation, and up to two missed cleavages. Peptides were considered to be identified if their MASCOT individual ion score was higher than the MASCOT identity scores ($p<0.05$).

Example 7

A Double-Blind, Randomized Study Comparing the Combined Use of FUCA 2 Inhibitor and Clarithromycin/Omeprazole to Clarithromycin/Omeprazole in a Subject Infected with *H. pylori*.

This is a double blind; randomized trial examining combination therapy versus conventional therapy (clarithromycin/omeprazole) with short term (e.g. not more than 3 weeks) follow-up on the last subject randomized. All subjects will remain on therapy until the last subject completes the study. All subjects will then be transitioned, based on the findings, to open label of combination with continued follow-up or some recommendation about conventional therapy. The primary interest is in combination therapy. Therefore, a two-group combination versus conventional therapeutic agents concept will be used—splitting the population into conventional therapeutic agents and combination therapy equally. The conventional therapeutic agents arm is divided into two groups, FUCA 2 inhibitor and clarithromycin/omeprazole providing for 3 treatment arms: FUCA 2 inhibitor and clarithromycin/omeprazole (50% of the subjects), FUCA2 inhibitor and placebo (25% of the subjects) and clarithromycin/omeprazole and placebo (25% of the subjects).

Example 8

Secretion of FUCA2 in *Helicobacter pylori* Strains that are Resistant to Antibiotics FUCA2 was secreted upon the infection of *Helicobacter pylori* strains that are resistant to antibiotics. Human Capan 1 cells (cell number: $6 \times 10^7$) were infected with three *H. pylori* strains that are resistant to the treatment of Amoxicillin, Clarithromycin or Levofloxacin (MOI of 400) for 5 h. *H. pylori* was grown for 3 days under microaerobic conditions (containing 5% $O_2$, 10% $CO_2$, and 85% $N_2$) at 37° C. on trypticase soy agar II plates supplemented with 5% sheep's blood. The bacterial cells were collected by gentle scrapping with a rubber policeman by centrifugation at 10,000×g at room temperature for 5 min. The resulting cells were suspended in DMEM at a suitable concentration for further studies without any additives. Cancer cells were grown to confluency in tissue culture dishes. The monolayer of each cancer cell line was washed twice with DMEM. *H. pylori* was added to cancer cells at an MOI of approximately 400 per cell and incubated at 37° C. with DMEM in a 5% CO2 incubator for a total of 4 or 8 h. An identical amount of *H. pylori* or cancer cells was cultured individually in a culture dish as the negative control. After 1 h of co-incubation, the *H. pylori*-cancer cell coculture was washed twice with DMEM to remove unattached *H. pylori* and debris. DMEM wash medium was pre-warmed at 37° C. to avoid stressing either the *H. pylori* or cancer cells. Tight attachment of *H. pylori* to cancer cells was achieved after 1 h.

After washing, incubation was continued for an additional 3 or 7 h. At the end of the incubation, the coculture was washed 2 times with PBS (PBS, pH 7.4) at 37° C. to remove unattached *H. pylori*. All of the control experiments were treated in a similar manner.

Activity Assay of α-L-fucosidase. Cell culture supernatants, obtained from (i) culture of *H. pylori* (~$2 \times 10^{10}$ cells), (ii) culture of cancer cells (~$1 \times 10^8$ cells), or (iii) co-cultured *H. pylori*-cancer cells (MOI=400:1), were incubated in serum-free DMEM for 4 or 8 h. After removing cell debris, the conditioned media containing secreted proteins were collected, concentrated to approximately 10-fold using an Amicon Ultra-15 centrifugal filter (Millipore; 30-kDa cut-off), and dialyzed in 50 mM HEPES pH 8.0. The concentrated solutions were subjected to the activity assay of α-L-fucosidase. Each assay (200 mL) contained 50 mM HEPES (pH 8.0), 30 mM 4-methylumbelliferylaa-L-fucoside, and 20 mL α-L-fucosidase (enriched from co-cultured media). The emission at 465 nm was monitored with an excitation wavelength of 360 nm to measure the release of fluorescent 4-methylumbelliferone at 20° C.

An activity of 1.17-2.52 nmol/min was obtained per mL of co-cultured media under the aforementioned condition in each of the three *H. pylori* antibiotic resistant strains.

All patents and other references cited in the specification are indicative of the level of skill of those skilled in the art, and are incorporated by reference in their entireties, including any tables and figures, to the same extent as if each reference had been incorporated by reference in its entirety individually.

One skilled in the art would readily appreciate that the compositions and methods are well adapted to obtain the ends and advantages mentioned, as well as those inherent therein. The methods, variances, and compositions described herein as presently representative of preferred embodiments are exemplary and are not intended as limitations on the scope. Changes therein and other uses will occur to those skilled in the art, which are encompassed within the spirit of the invention, are defined by the scope of the claims.

Definitions provided herein are not intended to be limiting from the meaning commonly understood by one of skill in the art unless indicated otherwise.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims. Thus, it should be understood that although aspects of the present invention have been specifically disclosed by preferred embodiments and optional features, modification and variation of the embodiments herein disclosed may be resorted to by those skilled in the art, and that such modifications and variations are considered to be within the scope of aspects of this invention.

The invention has been described broadly and generically herein. Each of the narrower species and subgeneric groupings falling within the generic disclosure also form part of aspects of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of inhibiting or arresting development of an infection caused by a Helicobacter pylori strain, the method comprising:
    administering to a subject in need thereof a pharmaceutical composition comprising a therapeutically effective amount of an α-L-fucosidase 2 inhibitor, and
a pharmaceutically acceptable carrier, excipient or diluent; wherein
    the Helicobacter pylori strain is resistant to Amoxicillin, Clarithromycin or Levofloxacin.

2. A method of inhibiting or arresting developing of an infection caused by a Helicobacter pylori strain, the method comprising:
    selecting a subject infected with or suspected of being infected with a Helicobacter pylori strain that is resistant to Amoxicillin, Clarithromycin or Levofloxacin; and
    administering to the subject a therapeutically effective amount of an α-L-fucosidase 2 inhibitor.

3. The method of claim 2, wherein the subject has a condition selected from the group consisting of chronic superficial gastritis, gastric ulcer, duodenal ulcer, gastric adenocarcinoma, non-Hodgkin lymphoma in human stomach, liver disease, colorectal disease, pancreatic disease, skin disease, heart disease, and autoimmune diseases.

4. The method of claim 3 wherein the condition is autoimmune disease and the autoimmune disease is autoimmune gastritis, pernicious anemia or non-steroid anti-inflammatory drug (NSAID) related gastric disease.

5. The method of claim 2, wherein the α-L-fucosidase 2 inhibitor is fuconojirimycin or an analog thereof, wherein the analog has the structure of the formula:

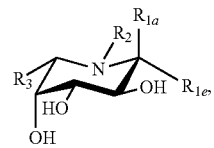

in which $R_{1a}$, $R_{1e}$, $R_2$ and $R_3$ are independently H, alkyl, alkenyl, alkynyl, acyl, aryl, arylalkyl, or arylacyl or a heteroatom form thereof.

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Homo sapiens
```

<400> SEQUENCE: 1

Tyr Glu Asp Phe Gly Pro Leu Phe Thr Ala Lys
 1               5                  10

<210> SEQ ID NO 2
<211> LENGTH: 8
<212> TYPE: PRT
<213> ORGANISM: Homo sapiens

<400> SEQUENCE: 2

Gln Leu Pro Ala Trp Phe Phe Gln
 1               5

<210> SEQ ID NO 3
<211> LENGTH: 447
<212> TYPE: PRT
<213> ORGANISM: Homo sapiens

<400> SEQUENCE: 3

Met Arg Pro Gln Glu Leu Pro Arg Leu Ala Phe Pro Leu Leu Leu
 1               5                  10                  15

Leu Leu Leu Leu Leu Pro Pro Pro Cys Pro Ala His Ser Ala Thr
                 20                  25                  30

Arg Phe Asp Pro Thr Trp Glu Ser Leu Asp Ala Arg Gln Leu Pro Ala
                 35                  40                  45

Trp Phe Asp Gln Ala Lys Phe Gly Ile Phe Ile His Trp Gly Val Phe
         50                  55                  60

Ser Val Pro Ser Phe Gly Ser Glu Trp Phe Trp Tyr Trp Gln Lys
65                  70                  75                  80

Glu Lys Ile Pro Lys Tyr Val Glu Phe Met Lys Asp Asn Tyr Pro Pro
                 85                  90                  95

Ser Phe Lys Tyr Glu Asp Phe Gly Pro Leu Phe Thr Ala Lys Phe Phe
                100                 105                 110

Asn Ala Asn Gln Trp Ala Asp Ile Phe Gln Ala Ser Gly Ala Lys Tyr
                115                 120                 125

Ile Val Leu Thr Ser Lys His His Glu Gly Phe Thr Leu Trp Gly Ser
                130                 135                 140

Glu Tyr Ser Trp Asn Trp Asn Ala Ile Asp Glu Gly Pro Lys Arg Asp
145                 150                 155                 160

Ile Val Lys Glu Leu Glu Val Ala Ile Arg Asn Arg Thr Asp Leu Arg
                165                 170                 175

Phe Gly Leu Tyr Tyr Ser Leu Phe Glu Trp Phe His Pro Leu Phe Leu
                180                 185                 190

Glu Asp Glu Ser Ser Ser Phe His Lys Arg Gln Phe Pro Val Ser Lys
                195                 200                 205

Thr Leu Pro Glu Leu Tyr Glu Leu Val Asn Asn Tyr Gln Pro Glu Val
                210                 215                 220

Leu Trp Ser Asp Gly Asp Gly Gly Ala Pro Asp Gln Tyr Trp Asn Ser
225                 230                 235                 240

Thr Gly Phe Leu Ala Trp Leu Tyr Asn Glu Ser Pro Val Arg Gly Thr
                245                 250                 255

Val Val Thr Asn Asp Arg Trp Gly Ala Gly Ser Ile Cys Lys His Gly
                260                 265                 270

Gly Phe Tyr Thr Cys Ser Asp Arg Tyr Asn Pro Gly His Leu Leu Pro
                275                 280                 285

```
His Lys Trp Glu Asn Cys Met Thr Ile Asp Lys Leu Ser Trp Gly Tyr
            290                 295                 300
Arg Arg Glu Ala Gly Ile Ser Asp Tyr Leu Thr Ile Glu Glu Leu Val
305                 310                 315                 320
Lys Gln Leu Val Glu Thr Val Ser Cys Gly Gly Asn Leu Leu Met Asn
                325                 330                 335
Ile Gly Pro Thr Leu Asp Gly Thr Ser Ile Val Val Phe Glu Glu Arg
            340                 345                 350
Leu Arg Gln Val Gly Ser Trp Leu Lys Val Asn Gly Glu Ala Ile Tyr
                355                 360                 365
Glu Thr Tyr Thr Trp Arg Ser Gln Asn Asp Thr Val Thr Pro Asp Val
370                 375                 380
Trp Tyr Thr Ser Lys Pro Lys Glu Lys Leu Val Tyr Ala Ile Phe Leu
385                 390                 395                 400
Lys Trp Pro Thr Ser Gly Gln Leu Phe Leu Gly His Pro Lys Ala Ile
                405                 410                 415
Leu Gly Ala Thr Glu Val Lys Leu Leu Gly His Gly Pro Leu Asn
                420                 425                 430
Trp Ile Ser Leu Glu Gln Asn Gly Ile Met Val Glu Leu Pro Gln
            435                 440                 445

<210> SEQ ID NO 4
<211> LENGTH: 447
<212> TYPE: PRT
<213> ORGANISM: Homo sapiens

<400> SEQUENCE: 4

Met Arg Ala Pro Gly Met Arg Ser Arg Pro Ala Gly Pro Ala Leu Leu
1               5                   10                  15
Leu Leu Leu Leu Phe Leu Gly Ala Ala Glu Ser Val Arg Arg Ala Gln
                20                  25                  30
Pro Pro Arg Arg Tyr Thr Pro Asp Trp Pro Ser Leu Asp Ser Arg Pro
            35                  40                  45
Leu Pro Ala Trp Phe Asp Glu Ala Lys Phe Gly Val Phe Ile His Trp
50                  55                  60
Gly Val Phe Ser Val Pro Ala Trp Gly Ser Glu Trp Phe Trp Trp His
65                  70                  75                  80
Trp Gln Gly Glu Gly Arg Pro Gln Tyr Gln Arg Phe Met Arg Asp Asn
                85                  90                  95
Tyr Pro Pro Gly Phe Ser Tyr Ala Asp Phe Gly Pro Gln Phe Thr Ala
            100                 105                 110
Arg Phe Phe His Pro Glu Glu Trp Ala Asp Leu Phe Gln Ala Ala Gly
        115                 120                 125
Ala Lys Tyr Val Val Leu Thr Thr Lys His His Glu Gly Phe Thr Asn
        130                 135                 140
Trp Pro Ser Pro Val Ser Trp Asn Trp Asn Ser Lys Asp Val Gly Pro
145                 150                 155                 160
His Arg Asp Leu Val Gly Glu Leu Gly Thr Ala Leu Arg Lys Arg Asn
                165                 170                 175
Ile Arg Tyr Gly Leu Tyr His Ser Leu Leu Glu Trp Phe His Pro Leu
            180                 185                 190
Tyr Leu Leu Asp Lys Lys Asn Gly Phe Lys Thr Gln His Phe Val Ser
        195                 200                 205
Ala Lys Thr Met Pro Glu Leu Tyr Asp Leu Val Asn Ser Tyr Lys Pro
        210                 215                 220
```

```
Asp Leu Ile Trp Ser Asp Gly Glu Trp Glu Cys Pro Asp Thr Tyr Trp
225                 230                 235                 240

Asn Ser Thr Asn Phe Leu Ser Trp Leu Tyr Asn Asp Ser Pro Val Lys
                245                 250                 255

Asp Glu Val Val Val Asn Asp Arg Trp Gly Gln Asn Cys Ser Cys His
            260                 265                 270

His Gly Gly Tyr Tyr Asn Cys Glu Asp Lys Phe Lys Pro Gln Ser Leu
            275                 280                 285

Pro Asp His Lys Trp Glu Met Cys Thr Ser Ile Asp Lys Phe Ser Trp
    290                 295                 300

Gly Tyr Arg Arg Asp Met Ala Leu Ser Asp Val Thr Glu Glu Ser Glu
305                 310                 315                 320

Ile Ile Ser Glu Leu Val Gln Thr Val Ser Leu Gly Gly Asn Tyr Leu
                325                 330                 335

Leu Asn Ile Gly Pro Thr Lys Asp Gly Leu Ile Val Pro Ile Phe Gln
            340                 345                 350

Glu Arg Leu Leu Ala Val Gly Lys Trp Leu Ser Ile Asn Gly Glu Ala
        355                 360                 365

Ile Tyr Ala Ser Lys Pro Trp Arg Val Gln Trp Glu Lys Asn Thr Thr
    370                 375                 380

Ser Val Trp Tyr Thr Ser Lys Gly Ser Ala Val Tyr Ala Ile Phe Leu
385                 390                 395                 400

His Trp Pro Glu Asn Gly Val Leu Asn Leu Glu Ser Pro Ile Thr Thr
            405                 410                 415

Ser Gly Thr Thr Lys Ile Thr Met Leu Gly Ile Gln Gly Asp Leu Lys
            420                 425                 430

Trp Ser Thr Asp Pro Asp Lys Gly Leu Phe Ile Ser Leu Pro Gln
            435                 440                 445
```